(12) United States Patent
Ishizaki et al.

(10) Patent No.: US 9,839,648 B2
(45) Date of Patent: Dec. 12, 2017

(54) COMBINED ANTI-ACID-FAST BACTERIAL AGENT, SCREENING METHOD FOR ANTI-ACID-FAST BACTERIAL AGENTS, AND ACTIVITY INHIBITOR OF WECA OR ORTHOLOG THEREOF

(71) Applicants: MICROBIAL CHEMISTRY RESEARCH FOUNDATION, Tokyo (JP); COLORADO STATE UNIVERSITY RESEARCH FOUNDATION, Fort Collins, CO (US)

(72) Inventors: Yoshimasa Ishizaki, Tokyo (JP); Masayuki Igarashi, Tokyo (JP); Patrick Joseph Brennan, Fort Collins, CO (US); Dean Calvin Crick, Fort Collins, CO (US)

(73) Assignees: MICROBIAL CHEMISTRY RESEARCH FOUNDATION, Tokyo (JP); COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 70 days.

(21) Appl. No.: 14/895,719

(22) PCT Filed: Jun. 3, 2014

(86) PCT No.: PCT/JP2014/064682
§ 371 (c)(1),
(2) Date: Dec. 3, 2015

(87) PCT Pub. No.: WO2014/196512
PCT Pub. Date: Dec. 11, 2014

(65) Prior Publication Data
US 2016/0129035 A1 May 12, 2016

Related U.S. Application Data

(60) Provisional application No. 61/830,857, filed on Jun. 4, 2013.

(51) Int. Cl.
| | |
|---|---|
| *A61K 31/7052* | (2006.01) |
| *C07H 19/067* | (2006.01) |
| *A61K 31/7072* | (2006.01) |
| *A61K 45/06* | (2006.01) |
| *C12Q 1/04* | (2006.01) |
| *A61K 31/496* | (2006.01) |
| *C12Q 1/18* | (2006.01) |

(52) U.S. Cl.
CPC ........ *A61K 31/7072* (2013.01); *A61K 31/496* (2013.01); *A61K 31/7052* (2013.01); *A61K 45/06* (2013.01); *C07H 19/067* (2013.01); *C12Q 1/04* (2013.01); *C12Q 1/18* (2013.01)

(58) Field of Classification Search
None
See application file for complete search history.

(56) References Cited

U.S. PATENT DOCUMENTS

| | | |
|---|---|---|
| 6,780,616 B1 | 8/2004 | Takeuchi et al. |
| 2006/0178319 A1 | 8/2006 | Miyake et al. |
| 2009/0209744 A1 | 8/2009 | Takahashi et al. |
| 2011/0237530 A1 | 9/2011 | Takahashi et al. |

FOREIGN PATENT DOCUMENTS

| | | |
|---|---|---|
| CN | 101984047 | 3/2011 |
| EP | 1211259 | 6/2002 |
| JP | 2010-83847 | 4/2010 |
| WO | 0112643 | 2/2001 |
| WO | 2004067544 | 8/2004 |
| WO | 2008020560 | 2/2008 |
| WO | 2010038874 | 4/2010 |

OTHER PUBLICATIONS

Winn et al., "Antimicrobial nucleoside antibiotics targeting cell wall assembly: Recent advances in structure-function studies and nucleoside biosynthesis" Natural Product Reports (2010) vol. 27 pp. 279-304.*
International search report for International application No. PCT/JP2014/064682, dated Sep. 16, 2014 (6 pages).
Takahashi et al.: "Novel semisynthetic antibiotics from caprazamycins A—G: caprazene derivatives and their antibacterial activity"; The journal of Antibiotics, 2013, vol. 66, No. 3, pp. 171-178.
Jin et al.: "*Mycobacterium tuberculosis* Rv1302 ad *Mycobacterium smegmatis* MSMEG_4947 have WecA function and MSMEG_4947 is required for the growth of *M.smegmatis*"; FEMS Microbiology Letters, 2010, vol. 310, Issue 1, pp. 54-61.
Supplementary European Search Report issued in corresponding European Application No. 14807892.6 dated Feb. 13, 2017 (12 pages).
Campbell et al.: "Synthetic lethal compound combinations reveal a fundamental connection between wall teichoic acid and peptidoglycan biosyntheses in *Staphylococcus aureus*"; ACS Chemical Biology, 2011, vol. 6, No. 1, pp. 106-116.

(Continued)

*Primary Examiner* — Eric Olson
(74) *Attorney, Agent, or Firm* — Hamre, Schumann, Mueller & Larson, P.C.

(57) ABSTRACT

A drug combination against acid-fast bacillus, including: an inhibitor for WecA or an ortholog thereof; and at least one of an inhibitor for MurX or an ortholog thereof and an RNA synthesis inhibitor, wherein the inhibitor for WecA or an ortholog thereof is used in combination with the at least one of an inhibitor for MurX or an ortholog thereof and an RNA synthesis inhibitor; a screening method for a drug against acid-fast bacillus; and an inhibitor for WecA or an ortholog thereof.

2 Claims, 11 Drawing Sheets

(56) References Cited

OTHER PUBLICATIONS

Kimura et al.: "Selective Inhibition of the Bacterial Peptidoglycan Biosynthesis by the New Types of Lipcsidomycins"; The Journal of Antibiotics, 21998, vol. 51, No. 12, pp. 1099-1104.
Ishizaki et al.: "Inhibition of the First Step in Synthesis of the Mycobacterial Cell Wall Core, Catalyzed by the GlcNAc-1-phosphate Transferase WecA, by the Novel Caprazamycin Derivative CPZEN-45", 2013, vol. 288, No. 42, pp. 30309-30319.

* cited by examiner $^1$H-NMR spectrum of CPZEN-45 trifluoroacetate (in D$_2$O)

SEQUENCE LISTING

<160> NUMBER OF SEQ ID NOS: 12

<210> SEQ ID NO 1
<211> LENGTH: 1215
<212> TYPE: DNA
<213> ORGANISM: Mycobacterium tuberculosis

<400> SEQUENCE: 1

```
gtgcagtacg gtctcgaggt gtccagcgat gtggccggcg ttgccggtgg cttgctcgcc      60
ctgtcctatc gcggcgccgg tgtcccgctg cgtgagcttg cgctggtcgg gctgaccgcg     120
gcgatcatca cctattttgc gaccggtccg gtgcggatgc tggccagtcg cctgggagcc     180
gtcgcctacc cgcgggagcg agatgtgcac gtcacgccta cccctcggat gggtgggttg     240
gcgatgttcc tgggcattgt cggcgccgtc tttcttgcct cccagcttcc ggcactcacc     300
cgggggttcg tctattccac cggcatgccc gcggtgctgg tggccggtgc ggtgatcatg     360
ggcatcggcc tgatcgatga tcgttggggt ctggatgcac tgacgaagtt cgccggccag     420
atcacggcgg cgagcgttct ggtcaccatg ggtgtcgcct ggagtgtcct gtacatcccg     480
gtgggtggtg tgggcaccat cgtcttggac caggcttcct cgatcctgct taccctggcg     540
ctgaccgttt cgatcgtcaa cgcgatgaac tttgtcgacg gtctcgacgg gctggccgcc     600
ggcctgggcc tgataacggc gctggcaatc tgcatgttct cggtgggttt gcttcgtgac     660
cacggtggtg acgttttgta ctacccgccg gcggtgattt cggtggtcct ggccggggcc     720
tgcctgggct ttctgccaca caacttccac cgggccaaga tcttcatggg cgattccggg     780
tcgatgctga tcggcctgat gctggccgcc gcttccacca ccgcggccgg gccgatctcg     840
cagaacgcct acgcgctcg tgatgtattt gctttgctgt cgccgttcct gctggtggtg     900
gcggtcatgt ttgtgccaat gctcgacctg ctgctagcga tcgtccgtcg cacccgcgcc     960
ggccgcagcg cgtttagccc ggacaaaatg cacctgcatc accggctgct gcagatcggt    1020
cattcccatc ggcgcgtggt cctgatcatc tacctgtggg tgggcatcgt tgccttcggc    1080
gccgcgagct cgatcttctt taacccgcgc gacaccgcgg cggtgatgct gggcgcgatc    1140
gtggtcgccg gcgtcgcgac actgatcccc ctgttgcgcc gcggcgacga ctactacgac    1200
ccggacctgg actag                                                     1215
```

<210> SEQ ID NO 2
<211> LENGTH: 1215
<212> TYPE: DNA
<213> ORGANISM: Mycobacterium bovis

<400> SEQUENCE: 2

```
gtgcagtacg gtctcgaggt gtccagcgat gtggccggcg ttgccggtgg cttgctcgcc      60
ctgtcctatc gcggcgccgg tgtcccgctg cgtgagcttg cgctggtcgg gctgaccgcg     120
gcgatcatca cctattttgc gaccggtccg gtgcggatgc tggccagtcg cctgggagcc     180
gtcgcctacc cgcgggagcg agatgtgcac gtcacgccta cccctcggat gggtgggttg     240
gcgatgttcc tgggcattgt cggcgccgtc tttcttgcct cccagcttcc ggcactcacc     300
cgggggttcg tctattccac cggcatgccc gcggtgctgg tggccggtgc ggtgatcatg     360
ggcatcggcc tgatcgatga tcgttggggt ctggatgcac tgacgaagtt cgccggccag     420
atcacggcgg cgagcgttct ggtcaccatg ggtgtcgcct ggagtgtcct gtacatcccg     480
gtgggtggtg tgggcaccat cgtcttggac caggcttcct cgatcctgct taccctggcg     540
ctgaccgttt cgatcgtcaa cgcgatgaac tttgtcgacg gtctcgacgg gctggccgcc     600
ggcctgggcc tgataacggc gctggcaatc tgcatgttct cggtgggttt gcttcgtgac     660
cacggtggtg acgttttgta ctacccgccg gcggtgattt cggtggtcct ggccggggcc     720
tgcctgggct ttctgccaca caacttccac cgggccaaga tcttcatggg cgattccggg     780
```

```
tcgatgctga tcggcctgat gctggccgcc gcttccacca ccgcggccgg gccgatctcg    840
cagaacgcct acggcgctcg tgatgtattt gctttgctgt cgccgttcct gctggtggtg    900
gcggtcatgt ttgtgccaat gctcgacctg ctgctagcga tcgtccgtcg cacccgcgcc    960
ggccgcagcg cgtttagccc ggacaaaatg cacctgcatc accggctgct gcagatcggt   1020
cattcccatc ggcgcgtggt cctgatcatc tacctgtggg tgggcatcgg tgccttcggc   1080
gccgcgagct cgatcttctt taacccgcgc gacaccgcgg cggtgatgct gggcgcgatc   1140
gtggtcgccg gcgtcgcgac actgatcccc ctgttgcgcc gcggcgacga ctactacgac   1200
ccggacctgg actag                                                    1215
```

<210> SEQ ID NO 3
<211> LENGTH: 1221
<212> TYPE: DNA
<213> ORGANISM: Mycobacterium smegmatis

<400> SEQUENCE: 3

```
ttgctgcagt acggtgctcc ggtgatcacg gccacccgcg agaccggtat ggacagtcag     60
gtggtcctcg cgctgtcgga cacgggcgca ggtgtaccgc tgcgtgagct ggcgctcgtg    120
ggcctcaccg ccgcgatcat cacctacttc gcgacggggt gggtgagggt gctcgcgatc    180
cgcttcggcg ccgtggccta cccgcgcgaa cgcgacgtgc acgtgcagcc cacaccccgc    240
atgggcgggc tcgcgatgta catcggcgtc gcatcggcgg tgctgctggc atcccaactg    300
cccgcgctga cacgcggatt cgtgtactcg accggtatgc ccgcggtcgt ggtggcgggc    360
gggctcatca tggcgatcgg cctgatcgac gaccggtggg gcctggacgc gctgaccaag    420
ttcgcaggcc agatcaccgc cgcgagcgtg ctggtcacca tgggcgtggc gtggagcgtg    480
ctctacatcc cgatcggggg agtgggcacg atcgtgctcg accaggtctc ctcgatcctg    540
ctgacgctcg cgctgaccgt gtcgatcatc aacgcgatga acttcgtcga cggcctcgac    600
gggctcgcgg ccgcctcgg gctcatcacg gcgctgccca tctgcgtgtt ctcggtgggt    660
ctgctgcgcg accacggcgg cgacgtgctg ttctacccgc ccgcggtgat ctccgtggtg    720
ctcgcgggcg cctgcctggg gttcctgccg cacaacttcc accgcgccaa gatcttcatg    780
ggcgactccg gttcgatgct gatcgggctg atgctcggcg cggcctcgac caccgccgcg    840
ggccccatat cgcagaacgc ctacggcgcg cgcgacgtgt cgcactgtt gtcgccgttc    900 ctgctggtgg tcgccgtcat gctggtgccc gcgctggaca ccctgctcgc gatcgtgcgg    960
cgcacccgcg cgggccgcag cccgctgagt cccgacaaga tgcacctgca ccacaggttg   1020
ctgcagatcg gtcattccca ccgtcgcgcg gtgttgctga tctacctgtg ggtcgggatc   1080
atcgcgttcg gcgcggcaag cacgattttc ttcgatccgg gccagaccgc gatggtcatg   1140
ggagtggcca tcgtcgtggc gatcgtggtc acgctgatcc cgctgttgcg ccgcggtcca   1200
gacggtgcgc aggagccgtg a                                             1221
```

<210> SEQ ID NO 4
<211> LENGTH: 1077
<212> TYPE: DNA
<213> ORGANISM: Bacillus subtilis

<400> SEQUENCE: 4

```
atgcttgacg aacgcatgat tcgcattgtt gttgcgtttta ttgtctcgct gctgacagtt     60
ttaatcataa ccccaatcgt aaaaaggatt gcgattaaaa taggtgcagt tgaccagccc    120
agcaatcgaa aagtacatga caaaatcatg ccccgcatgg gcgggctggc catatttatc    180
```

```
ggggtggttg caggcgtgct tgcatccggt atttacacag aaacaaggat gacggcaatt       240
acagtcggag cattcatcat tattgtgtta ggtattcttg acgataaata tcaattaagt       300
gcaaaagtta agtttttgat tcaattaggt gtagccatta tgattgtaag cactggctta       360
aaaatggact ttttctcagt acctttttta acagaacgat tgagttagg atggatggct        420 tatccgctga cggtattatg gattgtcggc atcacgaacg caattaacct gattgatgga       480
ttggatggcc ttgctgccgg tctttctgtt atcggcctgt caacgattgc tgtcatggcg       540
ctatccggcg gaaaagtgct cattctgtca ctctcattag tcgttattgc cagcacgctg       600 gggttttgt tttacaactt ccatccggca aaaatcttta tgggagatac gggatcactg        660
tttttagggt atagtatctc gattctttca ttattaggcc tgtataaaag tgtcacattg       720
ttcagtatcg ttatcccgat tattatatta ggcgtaccga tttttgatac aacatttgct      780
atcatcagaa gaatattaaa caaacagccg atttcagcgc ctgataagtc gcatattcac      840
catagactga tggcctttgg cctttcacat cggatgtcgg tcttagttat ttatttaatt      900
ggatttattt tcagtatcag tgcgattgta cttaaaagtg ccacaatttg gctttctttg      960
tttattatct tcattttgat tatttttatg caaatcatag cagaagtgac aggactcgtg      1020
aatgaaaaat ttaagccgtt tacaaagttt tataaacggc tggtgaaaag gaattaa         1077
```

<210> SEQ ID NO 5
<211> LENGTH: 1080
<212> TYPE: DNA
<213> ORGANISM: Mycobacterium tuberculosis

<400> SEQUENCE: 5

```
atgaggcaga tccttatcgc cgttgccgta gcggtgacgg tgtccatctt gctgaccccg        60
gtgctgatcc ggttgttcac taagcagggc ttcggccacc agatccgtga ggatggcccg       120
cccagccacc acaccaagcg cggtacgccg tcgatgggcg gggtggcgat tctggccggc       180
atctgggcgg gctacctggg cgcccaccta gcgggcctgg cgtttgacgg tgaaggcatc       240
ggcgcatcgg tctgttggt gctgggccta gccaccgctt gggcggcgt cgggttcatc         300 gacgatctga tcaagatccg caggtcgcgc aatctcgggt tgaacaagac ggccaagacc       360
gtcgggcaga tcacctccgc cgtgctgttt ggcgtgctgg tgctgcagtt ccggaatgct       420
gccgccctga caccgggcag cgcggatctg tcctacgtgc gtgagatcgc caccgtcaca       480
ttggcgccgg tgctgttcgt gttgttctgc gtggtcatcg tcagcgcctg gtcgaacgcg       540
gtcaacttca ccgatggcct ggacgggctg ccgccggca ccatggcgat ggtcaccgcc        600
gcctacgtgc tgatcacctt ctggcagtac cgcaacgcgt gcgtgacggc gccgggcctg      660
ggctgctaca cgtgcgcgga cccgctggac ctggcgctca tcgcggccgc aaccgctggc      720
gcctgcatcg gttttttgtg gtggaacgcc gcgcccgcca agatcttcat gggtgacact      780
gggtcgctgg cgttgggcgg cgtcatcgcg gggttgtcgg tgaccagccg caccgagatc      840
cttgcggtgg tgctgggtgc gctgttcgtc gccgagatca cctcggtggt gttgcaaatc      900
ctgaccttcc ggaccaccgg gcgccggatg tttcggatgg cgcccttcca ccaccatttc      960
gagttggtcg gttgggctga aaccacggtc atcatccggt tctggctgct caccgcgatc     1020
acctgcggtc tgggcgtggc cttgttctac ggtgagtggc ttgccgcggt cggtgcctga     1080
```

<210> SEQ ID NO 6
<211> LENGTH: 1080
<212> TYPE: DNA

<213> ORGANISM: Mycobacterium bovis

<400> SEQUENCE: 6

| | | | | | |
|---|---|---|---|---|---|
| atgaggcaga | tccttatcgc | cgttgccgta | gcggtgacgg | tgtccatctt | gctgaccccg | 60 |
| gtgctgatcc | ggttgttcac | taagcagggc | ttcggccacc | agatccgtga | ggatggcccg | 120 |
| cccagccacc | acaccaagcg | cggtacgccg | tcgatgggcg | gggtggcgat | tctggccggc | 180 |
| atctgggcgg | gctacctggg | cgcccaccta | gcgggcctgg | cgtttgacgg | tgaaggcatc | 240 |
| ggcgcatcgg | gtctgttggt | gctgggccta | gccaccgctt | tgggcggcgt | cgggttcatc | 300 |
| gacgatctga | tcaagatccg | caggtcgcgc | aatctcgggt | tgaacaagac | ggccaagacc | 360 |
| gtcgggcaga | tcacctccgc | cgtgctgttt | ggcgtgctgg | tgctgcagtt | ccggaatgct | 420 |
| gccggcctga | caccgggcag | cgcggatctg | tcctacgtgc | gtgagatcgc | caccgtcaca | 480 |
| ttggcgccgg | tgctgttcgt | gttgttctgc | gtggtcatcg | tcagcgcctg | gtcgaacgcg | 540 |
| gtcaacttca | ccgatggcct | ggacgggctg | ccgccggca | ccatggcgat | ggtcaccgcc | 600 |
| gcctacgtgc | tgatcacctt | ctggcagtac | cgcaacgcgt | gcgtgacggc | gccgggcctg | 660 |
| ggctgctaca | cgtgcgcga | cccgctggac | ctggcgctca | tcgcggccgc | aaccgctggc | 720 |
| gcctgcatcg | gttttttgtg | gtggaacgcc | gcgcccgcca | agatcttcat | gggtgacact | 780 |
| gggtcgctgg | cgttgggcgg | cgtcatcgcg | gggttgtcgg | tgaccagccg | caccgagatc | 840 |
| cttgcggtgg | tgctgggtgc | gctgttcgtc | gccgagatca | cctcggtggt | gttgcaaatc | 900 |
| ctgaccttcc | ggaccaccgg | gcgccggatg | tttcggatgg | cgcccttcca | ccaccatttc | 960 |
| gagttggtcg | gttgggctga | aaccacggtc | atcatccggt | tctggctgct | caccgcgatc | 1020 |
| acctgcggtc | tgggcgtggc | cttgttctac | ggtgagtggc | ttgccgcggt | cggtgcctga | 1080 |

<210> SEQ ID NO 7
<211> LENGTH: 1080
<212> TYPE: DNA
<213> ORGANISM: Mycobacterium smegmatis

<400> SEQUENCE: 7

| | | | | | |
|---|---|---|---|---|---|
| atgatgctga | tcctcatcgc | cgtcggcatc | gcgcttgcgg | tctccatcct | gctgacgccc | 60 |
| gccctgatcc | ggctgttcac | caaacagggc | ctgggccacg | agatccggga | ggacgggccg | 120 |
| cccagccacg | ccaagaaacg | cggcacaccg | tcgatgggcg | gcgtcgcgat | cctcgccggc | 180 |
| atctgggccg | gctacctggg | cagccatctg | gtcggcatgg | cgatgggcgg | cgacgggccg | 240 |
| tccgcgtcgg | gcctgctggt | gctcgggctg | gcgaccgtgc | tcggtggcgt | cggcttcatc | 300 |
| gacgacatga | tcaagctcaa | gcgcgcccgc | aacctggggc | tgaacaagac | cgccaagacg | 360 |
| gtcgggcagt | tgttcgccgc | ggtgctgttc | ggtgtgctgg | cgttgcagtt | ccgcaacggc | 420 |
| gacggcctga | caccgggcag | cgccgagctg | tcctatgtgc | gtgagatcgc | cacggtcacg | 480 |
| ctggcccgg | ccttgttcgt | gctgttctgc | gtcgtggtgg | tcagcgcctg | gtccaacgcg | 540 |
| gtgaatttca | ccgacggtct | cgacgggctc | cggcggggcg | cgatggcgat | ggtcacggcg | 600 |
| gcatacgtgc | tgatcacgtt | ctggcagtac | cgcaacgcgt | gcgcgacggc | gccgggcctg | 660 |
| ggctgttaca | cgtgcgcga | cccgctggac | ctcgcacttg | tcgctgccgc | gacggcagga | 720 |
| gcgtgcgtgg | gcttcctgtg | gtggaacgcc | gcgccggcca | agatcttcat | gggcgacacc | 780 |
| ggatcgctgc | cgctcggcgg | catcatcgcg | ggcatctcgg | tcaccagccg | caccgagatc | 840 |
| ctcgcggtcg | tgctgggtgc | gctgttcgtc | gcagaggtca | cctcggtggt | ggtccagatc | 900 |
| ctggcgttcc | gcacgaccgg | gcgccgcgtg | ttccgcatgg | ccccgttcca | ccaccacttc | 960 |

```
gagctggtgg gatgggccga gacgcaggtg atcatccggt tctggctgct gacggccatc    1020
gcgtgtggtc tgggcgtggc cctgttctac ggcgagtggc tgacggccgt cggtgcctga    1080

<210> SEQ ID NO 8
<211> LENGTH: 975
<212> TYPE: DNA
<213> ORGANISM: Bacillus subtilis

<400> SEQUENCE: 8
atgcttgagc aagtcattct gtttacaatt ttaatggggt ttttaattag tgttctgctc      60
tctccgattc ttattccgtt tttaagaaga ttaaaattcg ccagagtat tagagaagaa     120 ggaccgaaat cacatcagaa aaaatcaggg acaccgacaa tgggcggggt catgatcata    180
ctttctatca tagtgacaac aattgttatg acacagaagt tttcagaaat aagccccgaa    240
atggtgctgc ttctgtttgt tacgctaggc tacggtttgc ttggcttttt agatgattac    300
atcaaggttg tcatgaagcg caatcttgga ttgacatcaa agcaaaagct gatcggacaa    360
attattattg cggttgtatt ttacgccgtg tatcattact acaattttgc gacggatatt    420
cgcattcctg gaactgactt atcatttgat cttggctggg cttactttat ccttgtgctc    480
tttatgctag tcggcggatc aaacgcagtt aacctgactg acggccttga cgggttatta    540
tccggtactg cggcgattgc ctttggcgcc tttgccattc tggcatggaa tcagtctcaa    600
tatgacgtag cgattttctc agttgccgtt gtcggtgcag ttctgggctt ccttgtattt    660
aatgctcatc cggccaaagt ttttatggga gatacgggat cgcttgcatt gggaggagcc    720
atcgttacca ttgccatttt aacgaaatta gagatcctgc tggttatcat cggcggtgta    780
ttcgttatcg agacattatc cgttattttg caggtcatca gctttaaaac gacaggtaaa    840
cgaatcttta aaatgagtcc gcttcatcac cattatgagc ttgtcggctg gtctgaatgg    900
agagtagtcg tgacgttttg ggctgcggga cttttgcttg ccgttttagg aatttacatc    960
gaggtgtggt tataa                                                      975

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
aggacatgaa acctatcagc ag                                               22

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
tctccgcaaa caacttcgat tc                                               22

<210> SEQ ID NO 11
<211> LENGTH: 22
<212> TYPE: DNA
<213> ORGANISM: Artificial Sequence
<220> FEATURE:
<223> OTHER INFORMATION: primer
```

```
<400> SEQUENCE: 11
ccggacacaa gattggaatt gc                                       22

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
agcagcacaa gctcaaacaa c                                        21
```

COMBINED ANTI-ACID-FAST BACTERIAL AGENT, SCREENING METHOD FOR ANTI-ACID-FAST BACTERIAL AGENTS, AND ACTIVITY INHIBITOR OF WECA OR ORTHOLOG THEREOF

TECHNICAL FIELD

The present invention relates to: a drug combination against acid-fast bacillus which is effective to acid-fast bacillus including tuberculosis bacteria; a screening method for a drug against acid-fast bacillus; and an inhibitor for WecA or an ortholog thereof.

BACKGROUND ART

Bacteria that show resistance to decolorization by hydrochloric acid alcohol after fixed and stained with, for example, fuchsine or Crystal violet are called acid-fast bacillus, acid-fast bacillus bacteria, etc.

The acid-fast bacillus includes bacteria belonging to the genus *Mycobacterium* such as tuberculosis bacteria (*Mycobacterium tuberculosis*).

Tuberculosis is an infectious disease caused by tuberculosis bacteria. Among infectious diseases worldwide, tuberculosis is a disease of which the largest number of people died as a single infection. In recent years, multidrug-resistant tuberculosis (MDR-TB) bacteria and extensively drug-resistant tuberculosis (XDR-TB) bacteria have been detected in the tuberculosis bacteria, raising a serious problem.

Hitherto, caprazamycins or derivatives thereof have been found as compounds having excellent antibacterial activity against acid-fast bacillus (see, for example, PTLs 1 to 4).

Among these proposed compounds, for example, CPZEN-45, which is a derivative of caprazamycin, has been found to have excellent antibacterial activity against multidrug-resistant tuberculosis (MDR-TB) bacteria and extensively drug-resistant tuberculosis (XDR-TB) bacteria.

Under such circumstances, studies have actively been made to develop a therapeutic drug against tuberculosis caused by tuberculosis bacteria included in acid-fast bacillus, and keen demand has arisen for provision of a more effective therapeutic drug.

CITATION LIST

Patent Literature

PTL 1: International Publication No. WO01/012643
PTL 2: International Publication No. WO2004/067544
PTL 3: International Publication No. WO2008/020560
PTL 4: Japanese Patent Application Laid-Open (JP-A) No. 2010-83847

SUMMARY OF INVENTION

Technical Problem

The present invention has been made in view of the above problems in the art and aims to achieve the following object. Specifically, an object of the present invention is to provide a drug combination against acid-fast bacillus which has excellent drug efficacy to acid-fast bacillus; a screening method for a drug against acid-fast bacillus; and an inhibitor for WecA or an ortholog thereof which has an excellent inhibitory activity against WecA or an ortholog thereof.

Solution to Problem

Means for solving the problems are as follows.

<1> A drug combination against acid-fast bacillus, including:
an inhibitor for WecA or an ortholog thereof, and
at least one of an inhibitor for MurX or an ortholog thereof and an RNA synthesis inhibitor,
wherein the inhibitor for WecA or an ortholog thereof is used in combination with the at least one of an inhibitor for MurX or an ortholog thereof and an RNA synthesis inhibitor.
<2> A screening method for a drug against acid-fast bacillus, the method including:
measuring activity of a test substance against WecA or an ortholog thereof.
<3> An inhibitor for WecA or an ortholog thereof, including:
a compound expressed by the following Structural Formula (1):

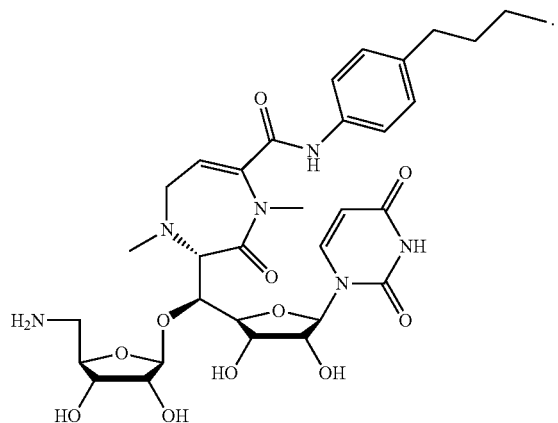

Structural Formula (1)

Advantageous Effects of Invention

The present invention can achieve the above object and provide a drug combination against acid-fast bacillus which has excellent drug efficacy to acid-fast bacillus; a screening method for a drug against acid-fast bacillus; and an inhibitor for WecA or an ortholog thereof which has an excellent inhibitory activity against WecA or an ortholog thereof.

DESCRIPTION OF EMBODIMENTS

Drug Combination Against Acid-Fast Bacillus

Figure 1:
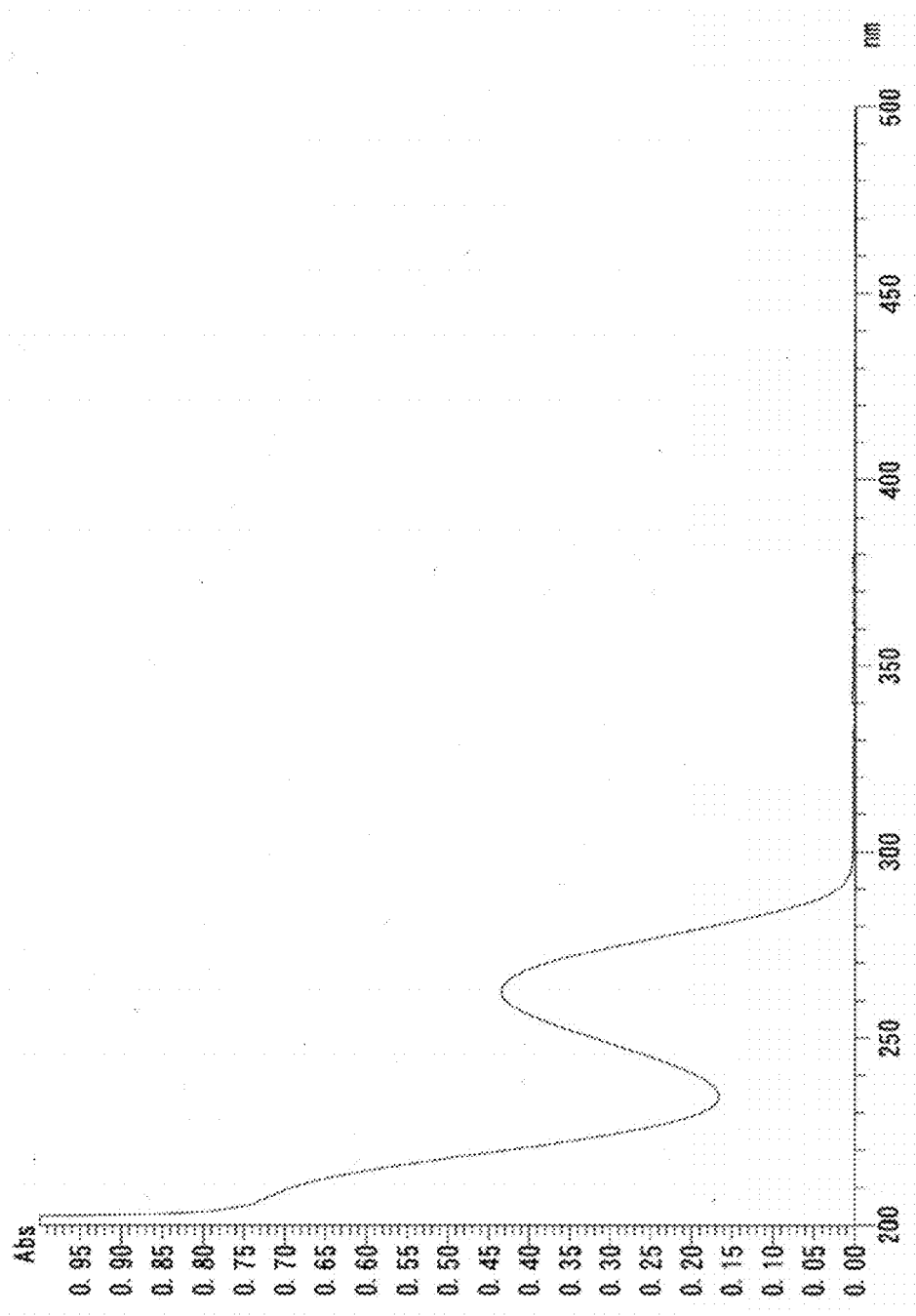
FIG. 1 is a chart of a UV absorption spectrum of a compound expressed by Structural Formula (2).

A drug combination against acid-fast bacillus of the present invention contains at least: an inhibitor for WecA or an ortholog thereof; and at least one of an inhibitor for MurX or an ortholog thereof and an RNA synthesis inhibitor. If necessary, the drug combination against acid-fast bacillus further contains other ingredients.

<Inhibitor for WecA or an Ortholog Thereof>

The inhibitor for WecA or an ortholog thereof in the drug combination against acid-fast bacillus contains at least a compound which inhibits activity of WecA or an ortholog thereof, and, if necessary, further contains other ingredients.

The WecA is an enzyme which tuberculosis bacteria (*Mycobacterium tuberculosis*) have (see SEQ ID NO: 1 for the nucleotide sequence thereof). The WecA is an enzyme involved with synthesis of mycolyl arabinogalactan which is a constituent component of a cell wall.

The ortholog refers to a cluster of genes considered to have a common ancestor gene. Examples of the ortholog of the WecA include: WecA that is an enzyme *Mycobacterium bovis* has (i.e., an enzyme involved with synthesis of mycolyl arabinogalactan which is a constituent component of a cell wall; see SEQ ID NO: 2 for the nucleotide sequence thereof); WecA that is an enzyme *Mycobacterium smegmatis* has (i.e., an enzyme involved with synthesis of mycolyl arabinogalactan which is a constituent component of a cell wall; see SEQ ID NO: 3 for the nucleotide sequence thereof); and TagO that is an enzyme *Bacillus subtilis* has (i.e., an enzyme involved with synthesis of teichoic acid which is a constituent component of a cell wall; see SEQ ID NO: 4 for the nucleotide sequence thereof).

—Compound which inhibits Activity of WecA or an Ortholog Thereof—

The compound which inhibits activity of WecA or an ortholog thereof is not particularly limited and may be appropriately selected depending on the intended purpose. Examples thereof include a compound expressed by the following Structural Formula (1) (hereinafter may be referred to as "CPZEN-45") and tunicamycin. These may be used alone or in combination of two or more thereof.

Among them, CPZEN-45 is preferred.

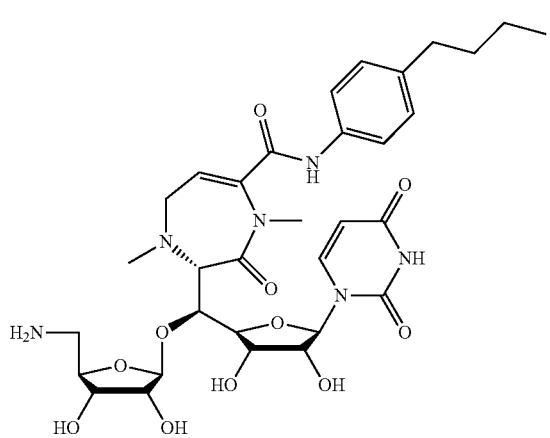

Structural Formula (1)

The CPZEN-45 and tunicamycin are known as a compound having antibacterial activity.

The compound which inhibits activity of WecA or an ortholog thereof may be in the form of salt.

The salt is not particularly limited and may be appropriately selected depending on the intended purpose so long as it is a pharmacologically acceptable salt. Examples thereof include organic salts such as acetate and citrate, hydrochloride and carbonate.

The compound which inhibits activity of WecA or an ortholog thereof may be obtained through chemical synthesis or may be obtained from a microorganism that produces it.

The production method for CPZEN-45 is not particularly limited and may be appropriately selected depending on the intended purpose. Examples thereof include the methods described in International Publication No. WO2004/067544 and JP-A No. 2010-83847.

The production method for tunicamycin is not particularly limited and may be appropriately selected depending on the intended purpose. Examples thereof include a method of producing it from a microorganism that produces tunicamycin.

The amount of the compound which inhibits activity of WecA or an ortholog thereof in the inhibitor for WecA or an ortholog thereof is not particularly limited and may be appropriately selected depending on the intended purpose. The inhibitor for WecA or an ortholog thereof may consist of the compound which inhibits activity of WecA or an ortholog thereof.

—Other Ingredients—

The other ingredients in the inhibitor for WecA or an ortholog thereof are not particularly limited and may be appropriately selected depending on the intended purpose from pharmacologically acceptable carriers. Examples thereof include additives, supplements and water. These may be used alone or in combination of two or more thereof.

The additives or supplements are not particularly limited and may be appropriately selected depending on the intended purpose. Examples thereof include a disinfectant, a preserving agent, a binding agent, a thickener, an adhesive agent, an integrating agent, a colorant, a stabilizer, a pH adjuster, a buffer, a tonicity agent, a solvent, an antioxidant, a UV rays-preventing agent, a preventing agent for precipitation of crystals, a defoaming agent, a property improving agent and an antiseptic agent.

The disinfectant is not particularly limited and may be appropriately selected depending on the intended purpose. Examples thereof include cationic surfactants such as benzalkonium chloride, benzethonium chloride and cetylpyridinium chloride.

The preserving agent is not particularly limited and may be appropriately selected depending on the intended purpose. Examples thereof include p-hydroxybenzoate esters, chlorobutanol and clesol.

The binding agent, thickener and adhesive agent are not particularly limited and may be appropriately selected depending on the intended purpose. Examples thereof include starch, dextrin, cellulose, methyl cellulose, ethyl cellulose, carboxymethyl cellulose, hydroxyethyl cellulose, hydroxypropyol cellulose, hydroxypropyolmethyl cellulose, carboxymethyl starch, pullulan, sodium alginate, ammonium alginate, propylene glycol alginic acid esters, guar gum, locust bean gum, gum Arabic, xanthane gum, gelatin, casein, polyvinyl alcohol, polyethylene oxide, polyethylene glycol, ethylene/propylene block polymers, sodium polyacrylates and polyvinylpyrrolidone.

The integrating agent is not particularly limited and may be appropriately selected depending on the intended purpose. Examples of the integrating agent include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate and polyvinylpyrrolidone.

The colorant is not particularly limited and may be appropriately selected depending on the intended purpose. Examples thereof include titanium oxide and iron oxide.

The stabilizer is not particularly limited and may be appropriately selected depending on the intended purpose. Examples thereof include tragacanth, gum Arabic, gelatin, sodium pyrosulfite, ethylenediaminetetraacetate (EDTA), thioglycolic acid and thiolactic acid.

The pH adjuster or the buffer is not particularly limited and may be appropriately selected depending on the intended purpose. Examples thereof include sodium citrate, sodium acetate and sodium phosphate.

The tonicity agent is not particularly limited and may be appropriately selected depending on the intended purpose. Examples thereof include sodium chloride and glucose.

The amount of the other ingredients in the inhibitor for WecA or an ortholog thereof is not particularly limited and may be appropriately selected depending on the intended purpose.

<At Least One of the Inhibitor for MurX or an Ortholog Thereof and the RNA Synthesis Inhibitor>

Either one or both of the inhibitor for MurX or an ortholog thereof and the RNA synthesis inhibitor may be used in the drug combination against acid-fast bacillus.

—Inhibitor for MurX or an Ortholog Thereof—

The inhibitor for the MurX or an ortholog thereof in the drug combination against acid-fast bacillus contains at least a compound which inhibits activity of MurX or an ortholog thereof, and, if necessary, further contains other ingredients.

The MurX is an enzyme which tuberculosis bacteria (*Mycobacterium tuberculosis*) have (see SEQ ID NO: 5 for the nucleotide sequence thereof). The MurX is an enzyme involved with synthesis of peptidoglycan which is a constituent component of a cell wall.

Examples of the ortholog of the MurX include: MraY that is an enzyme *Mycobacterium bovis* has (i.e., an enzyme involved with synthesis of peptidoglycan which is a constituent component of a cell wall; see SEQ ID NO: 6 for the nucleotide sequence thereof); MraY that is an enzyme *Mycobacterium smegmatis* has (i.e., an enzyme involved with synthesis of peptidoglycan which is a constituent component of a cell wall; see SEQ ID NO: 7 for the nucleotide sequence thereof); and MraY that is an enzyme *Bacillus subtilis* has (i.e., an enzyme involved with synthesis of peptidoglycan which is a constituent component of a cell wall; see SEQ ID NO: 8 for the nucleotide sequence thereof).

——Compound which Inhibits Activity of MurX or an Ortholog Thereof——

The compound which inhibits activity of MurX or an ortholog thereof is not particularly limited and may be appropriately selected depending on the intended purpose. Examples thereof include caprazamycins, liposidomycins, mureidomycins, pacidamycins, napsamycins, muraymycins, FR-900493, capuramycins, A-503083 and lysis protein E of bacteriophage φX174. These may be used alone or in combination of two or more thereof.

Among them, caprazamycin B, liposidomycin B, mureidomycin A, muraymycin A1, capuramycin and lysis protein E of bacteriophage φX174 are preferred, and caprazamycin B is more preferred.

The compound which inhibits activity of MurX or an ortholog thereof may be in the form of salt.

The salt is not particularly limited and may be appropriately selected depending on the intended purpose so long as it is a pharmacologically acceptable salt. Examples thereof include organic salts such as acetate and citrate, hydrochloride and carbonate.

The compound which inhibits activity of MurX or an ortholog thereof may be obtained through chemical synthesis or may be obtained from a microorganism that produces it.

The compound which inhibits activity of MurX or an ortholog thereof is a known compound, and the production method therefor is not particularly limited and may be appropriately selected from known methods.

The production method for caprazamycin B is not particularly limited and may be appropriately selected depending on the intended purpose. Examples thereof include a method of producing it using *Streptomyces* sp. MK730-62F2 strain deposited under accession number FERM BP-7218 described in International Publication No. WO01/012643.

The *Streptomyces* sp. MK730-62F2 strain was requested for deposition in the National Institute of Bioscience and Human-Technology Agency of Industrial Science and Technology (which is currently the Incorporated Administrative Agency, National Institute of Technology and Evaluation, Patent Microorganisms Depositary (zip code: 292-0818, 2-5-8, Kazusakamatari, Kisarazu-shi, Chiba 292-0818 Japan)) and was domestically deposited on Nov. 27, 1998 (FERM P-17067). After that, a request to transfer it to an international deposition under the Budapest Treaty was received on Jul. 12, 2000, and it was internationally deposited as accession number FERM BP-7218.

The amount of the compound which inhibits activity of MurX or an ortholog thereof in the inhibitor for MurX or an ortholog thereof is not particularly limited and may be appropriately selected depending on the intended purpose. The inhibitor for MurX or an ortholog thereof may consist of the compound which inhibits activity of MurX or an ortholog thereof.

——Other Ingredients——

The other ingredients in the inhibitor for MurX or an ortholog thereof are not particularly limited and may be appropriately selected depending on the intended purpose. Examples thereof include those similar to the other ingredients described for the inhibitor for WecA or an ortholog thereof.

The amount of the other ingredients in the inhibitor for MurX or an ortholog thereof is not particularly limited and may be appropriately selected depending on the intended purpose.

—RNA Synthesis Inhibitor—

The RNA synthesis inhibitor in the drug combination against acid-fast bacillus contains at least a compound which inhibits synthesis of RNA; and, if necessary, further contains other ingredients.

——Compound which Inhibits Synthesis of RNA——

The compound which inhibits synthesis of RNA is not particularly limited and may be appropriately selected depending on the intended purpose. Examples thereof include rifampicin, rifamycin SV and rifabutin. These may be used alone or in combination of two or more thereof.

Among them, rifampicin is preferred.

The compound which inhibits synthesis of RNA may be in the form of salt.

The salt is not particularly limited and may be appropriately selected depending on the intended purpose so long as it is a pharmacologically acceptable salt. Examples thereof include organic salts such as acetate and citrate, hydrochloride and carbonate.

The compound which inhibits synthesis of RNA may be obtained through chemical synthesis or may be obtained from a microorganism that produces it.

The compound which inhibits synthesis of RNA is a known compound, and the production method therefor is not particularly limited and may be appropriately selected from known methods.

The amount of the compound which inhibits synthesis of RNA in the RNA synthesis inhibitor is not particularly limited and may be appropriately selected depending on the intended purpose. The RNA synthesis inhibitor may consist of the compound which inhibits synthesis of RNA.

——Other Ingredients——

The other ingredients in the RNA synthesis inhibitor are not particularly limited and may be appropriately selected depending on the intended purpose. Examples thereof include those similar to the other ingredients described for the inhibitor for WecA or an ortholog thereof.

The amount of the other ingredients in the RNA synthesis inhibitor is not particularly limited and may be appropriately selected depending on the intended purpose.

<Other Ingredients>

The other ingredients in the drug combination against acid-fast bacillus are not particularly limited and may be appropriately selected depending on the intended purpose. Examples thereof include those similar to the other ingredients described for the inhibitor for WecA or an ortholog thereof.

The amount of the other ingredients in the drug combination against acid-fast bacillus is not particularly limited and may be appropriately selected depending on the intended purpose.

<Acid-Fast Bacillus>

The acid-fast bacillus is not particularly limited and may be appropriately selected depending on the intended purpose, but is preferably tuberculosis bacteria. The tuberculosis bacteria are not particularly limited and may be appropriately selected depending on the intended purpose.

<Use>

The combination of the inhibitor for WecA or an ortholog thereof and at least one of the inhibitor for MurX or an ortholog thereof and the RNA synthesis inhibitor is not particularly limited and may be appropriately selected depending on the intended purpose. A combination of CPZEN-45 and caprazamycin B and a combination of tunicamycin and rifampicin are preferred, and a combination of CPZEN-45 and caprazamycin B is more preferred.

The drug combination against acid-fast bacillus may contain the inhibitor for WecA or an ortholog thereof in combination with only at least one of the inhibitor for MurX or an ortholog thereof and the RNA synthesis inhibitor, or in combination with not only at least one of the inhibitor for MurX or an ortholog thereof and the RNA synthesis inhibitor but also a drug containing another ingredient as an active ingredient.

In the drug combination against acid-fast bacillus, a single drug of the inhibitor for WecA or an ortholog thereof and a single drug of at least one of the inhibitor for MurX or an ortholog thereof and the RNA synthesis inhibitor may be used in combination. Alternatively, the inhibitor for WecA or an ortholog thereof and at least one of the inhibitor for MurX or an ortholog thereof and the RNA synthesis inhibitor may be used in combination as a single drug (a compound drug).

<Dosage Form>

The dosage form of the drug combination against acid-fast bacillus, the inhibitor for WecA or an ortholog thereof, the inhibitor for MurX or an ortholog thereof or the RNA synthesis inhibitor is not particularly limited and may be appropriately selected depending on the intended purpose. Examples thereof include a solid preparation, a semi-solid preparation and a liquid preparation. The drug combination against acid-fast bacillus, the inhibitor for WecA or an ortholog thereof, the inhibitor for MurX or an ortholog thereof, or the RNA synthesis inhibitor having any of these dosage forms can be produced according to a routine method.

When a single drug of the inhibitor for WecA or an ortholog thereof and a single drug of at least one of the inhibitor for MurX or an ortholog thereof and the RNA synthesis inhibitor are used in combination in the drug combination against acid-fast bacillus, their dosage forms are not particularly limited and may be appropriately selected depending on the intended purpose. Both of the inhibitors may have the same dosage form or different dosage forms.

—Solid Preparation—

The solid preparation is not particularly limited and may be appropriately selected depending on the intended purpose. When it is used as an internal preparation, examples of the solid preparation include tablets, chewable tablets, foaming tablets, orally-disintegrating tablets, troches, drops, hard capsules, soft capsules, granules, powder, pills, dry syrups and infusions.

When the solid preparation is an external preparation, examples of the solid preparation include suppositories, cataplasms and plasters.

—Semi-Solid Preparation—

The semi-solid preparation is not particularly limited and may be appropriately selected depending on the intended purpose. When it is used as an internal preparation, examples of the semi-solid preparation include electuaries, chewing gums, whip and jelly.

When the semi-solid preparation is used as an external preparation, examples of the semi-solid preparation include ointments, cream, mousse, inhaler and nasal gel.

—Liquid Preparation—

The liquid preparation is not particularly limited and may be appropriately selected depending on the intended purpose. When it is used as an internal preparation, examples of the liquid preparation include syrups, drinks, suspensions and spirits.

When the liquid preparation is used as an external preparation, examples of the liquid preparation include liquid, eye drops, aerosol and sprays.

<Administration>

The administration method, administration dose, administration period and administration target of the drug combination against acid-fast bacillus, the inhibitor for WecA or an ortholog thereof, the inhibitor for MurX or an ortholog thereof, or the RNA synthesis inhibitor are not particularly limited and may be appropriately selected depending on the intended purpose.

Examples of the administration method include a local administration method, an enteral administration method and a parenteral administration method.

When a single drug of the inhibitor for WecA or an ortholog thereof and a single drug of at least one of the inhibitor for MurX or an ortholog thereof and the RNA synthesis inhibitor are used in combination in the drug combination against acid-fast bacillus, their administration method are not particularly limited and may be appropriately selected depending on the intended purpose. Both of the inhibitors may be administered by the same administration method or different administration methods.

The administration dose is not particularly limited and may be appropriately selected considering various factors of an administration target, such as the age, body weight, constitution, symptom and the presence or absence of administration of a drug containing other active ingredients.

The ratio of the administration dosage of the inhibitor for WecA or an ortholog thereof and the administration dosage of at least one of the inhibitor for MurX or an ortholog thereof and the RNA synthesis inhibitor in the drug combination against acid-fast bacillus is not particularly limited and may be appropriately selected depending on the intended purpose.

The administration period is not particularly limited and may be appropriately selected depending on the intended purpose.

The inhibitor for WecA or an ortholog thereof and at least one of the inhibitor for MurX or an ortholog thereof and the RNA synthesis inhibitor in the drug combination against acid-fast bacillus may be administered at the same timing or different timings.

The animal species serving as the administration target is not particularly limited and may be appropriately selected depending on the intended purpose. Examples thereof include human, monkey, pig, bovine, sheep, goat, dog, cat, mouse, rat and bird, with human being suitably used.

(Treatment Method)

When administered to an individual infected with acid-fast bacillus, the drug combination against acid-fast bacillus can treat the individual. Therefore, the present invention also relates to a method for treating an individual infected by acid-fast bacillus, including administering the drug combination against acid-fast bacillus to the individual.

This treatment method can suitably used for tuberculosis bacteria among the acid-fast bacillus.

(Screening Method for a Drug Against Acid-Fast Bacillus)

A screening method for a drug against acid-fast bacillus of the present invention contains at least an activity measuring step and, if necessary, further contains other steps.

<Activity Measuring Step>

The activity measuring step is a step of measuring activity of a test substance to WecA or an ortholog thereof.

The activity of a test substance to WecA or an ortholog thereof may be activity of inhibiting enzymatic activity of WecA or an ortholog thereof, or may be activity of suppressing expression of wecA gene or an ortholog gene thereof.

The test substance is not particularly limited and may be appropriately selected depending on the intended purpose. Examples thereof include compounds produced by microorganisms, derivatives of the compounds, plant extracts and proteins.

The method for measuring the activity of the test substance to the WecA or an ortholog thereof is not particularly limited and may be appropriately selected depending on the intended purpose. Examples thereof include a method of measuring the enzymatic activity of WecA or an ortholog thereof and a method of measuring the expression level of wecA gene or an ortholog gene thereof.

The method for measuring the enzymatic activity of WecA or an ortholog thereof is not particularly limited and may be appropriately selected depending on the intended purpose. Examples thereof include a method of measuring it using a disruption liquid of bacterial cells of a strain expressing the WecA or an ortholog thereof.

The strain expressing the WecA or an ortholog thereof is not particularly limited and may be appropriately selected depending on the intended purpose. Examples thereof include *Bacillus subtilis* to which the gene of the WecA or an ortholog thereof has been introduced. The method for introducing the gene of the WecA or an ortholog thereof is not particularly limited and may be appropriately selected from known methods. Examples thereof include a method of introducing, to *Bacillus subtilis*, a plasmid to which the gene of the WecA or an ortholog thereof has been inserted.

The method for preparing the disruption liquid is not particularly limited and may be appropriately selected from known methods so long as it can disrupt the bacterial cells.

The method for measuring the enzymatic activity of WecA or an ortholog thereof using the disruption liquid of bacterial cells is not particularly limited and may be appropriately selected depending on the intended purpose. In one employable method, a substrate for the WecA or an ortholog thereof is radioactively labeled. The radioactively labeled substrate is included in the disruption liquid of bacterial cells, followed by reaction. The reaction product is detected through thin-layer chromatography and autoradiography to measure the enzymatic activity of WecA or an ortholog thereof. Examples of the substrate include UDP-GlcNAc.

The method for measuring the expression level of wecA gene or an ortholog gene thereof is not particularly limited and may be appropriately selected depending on the intended purpose. In one exemplary method, a test substance is made to act on acid-fast bacillus having wecA gene or an ortholog gene thereof to measure the expression level of wecA gene or an ortholog thereof in the acid-fast bacillus.

The method for making the test substance act on the acid-fast bacillus is not particularly limited and may be appropriately selected depending on the intended purpose. Examples thereof include a method of including the test substance in a medium of the acid-fast bacillus.

The expression level of the wecA gene or an ortholog gene thereof may be an expression level of mRNA or an expression level of a protein.

The method for measuring the expression level of mRNA or the expression level of a protein may be appropriately selected from known methods. For example, the expression level of mRNA can be measured through real-time PCR, and the expression level of a protein can be measured through western blotting.

<Other Steps>

The other steps are not particularly limited and may be appropriately selected depending on the intended purpose. Examples thereof include an evaluating step.

The evaluating step is a step of evaluating whether the activity of the WecA or an ortholog thereof is inhibited by the test substance from the results obtained in the activity measuring step.

The method for evaluating whether the test substance inhibits the activity of the WecA or an ortholog thereof in the evaluating step is not particularly limited and may be appropriately selected depending on the intended purpose. For example, when the enzymatic activity of the WecA or an ortholog thereof or the expression level of the wecA gene or an ortholog gene thereof in the presence of the test substance is lower than that in the absence of the test substance (control) in the activity measuring step, the test substance can be evaluated as inhibiting the activity of the WecA or an ortholog thereof. The test substance is thought to be able to use as a drug against acid-fast bacillus.

Also, when the enzymatic activity of the WecA or an ortholog thereof or the expression level of the wecA gene or an ortholog gene thereof in the presence of the test substance is lower than that in the presence of at least one of CPZEN-45 and tunicamycin serving as a control in the activity measuring step, the test substance can be evaluated as inhibiting the activity of the WecA or an ortholog thereof more strongly than at least one of CPZEN-45 and tunicamycin. The test substance is thought to be able to be more useful as a drug against acid-fast bacillus.

The screening method for a drug against acid-fast bacillus can suitably be used as a screening method for a drug against tuberculosis bacteria.

(Inhibitor for WecA or an Ortholog Thereof)

The inhibitor for WecA or an ortholog thereof of the present invention contains at least a compound expressed by the following Structural Formula (1); and, if necessary, further contains other ingredients.

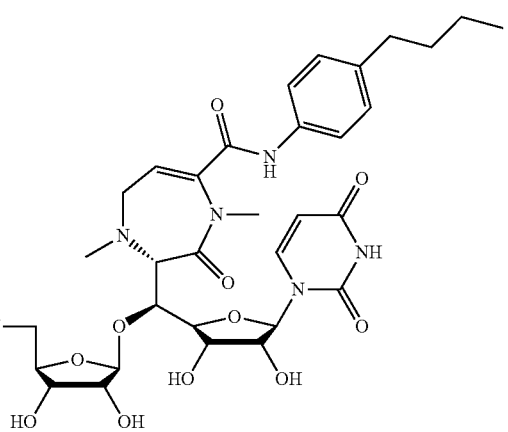

Structural Formula (1)

The WecA or an ortholog thereof is the same as described for the inhibitor for WecA or an ortholog thereof in the drug combination against acid-fast bacillus.

The compound expressed by Structural Formula (1) is CPZEN-45 and may be in the form of salt.

The salt is not particularly limited and may be appropriately selected depending on the intended purpose so long as it is a pharmacologically acceptable salt. Examples thereof include organic salts such as acetate and citrate, hydrochloride and carbonate.

The CPZEN-45 may be obtained through chemical synthesis or may be obtained from a microorganism that produces it.

The production method for the CPZEN-45 is not particularly limited and may be appropriately selected depending on the intended purpose. Examples thereof include those similar to the method described for the inhibitor for WecA or an ortholog thereof in the drug combination against acid-fast bacillus.

The amount of CPZEN-45 in the inhibitor for WecA or an ortholog thereof is not particularly limited and may be appropriately selected depending on the intended purpose. The inhibitor for WecA or an ortholog thereof may consist of the CPZEN-45.

In addition to the CPZEN-45, the inhibitor for WecA or an ortholog thereof may contain other compounds which inhibit activity of WecA or an ortholog thereof. The other compounds which inhibit activity of WecA or an ortholog thereof are not particularly limited and may be appropriately selected depending on the intended purpose. Examples thereof include tunicamycin.

The other ingredients in the inhibitor for WecA or an ortholog thereof are not particularly limited and may be appropriately selected depending on the intended purpose. Examples thereof include those similar to the other ingredients described for the inhibitor for WecA or an ortholog thereof in the drug combination against acid-fast bacillus.

The amount of the other ingredients in the inhibitor for WecA or an ortholog thereof is not particularly limited and may be appropriately selected depending on the intended purpose.

<Application>

Since the inhibitor for WecA or an ortholog thereof has excellent inhibitory effect against activity of WecA or an ortholog thereof, it can suitably be used as, for example, an active ingredient of the above-described drug combination against acid-fast bacillus of the present invention. Also, the inhibitor for WecA or an ortholog thereof can suitably be used as, for example, a reagent used for an index of the above-described screening method for a drug against acid-fast bacillus of the present invention.

EXAMPLES

The present invention will next be described in detail by way of Production Examples and Test Examples, which should not be construed as limiting the present invention thereto.

Production Example 1

<Production of Compound Expressed by Structural Formula (2)>

The compound expressed by the Structural Formula (2) (caprazamycin B) was produced in the same manner as in Example 1 of International Publication No. WO01/012643 using *Streptomyces* sp. MK730-62F2 strain deposited under accession number FERM BP-7218.

——Physico-Chemical Properties of Caprazamycin B——

Physico-chemical properties of caprazamycin B are as follows, confirming that caprazamycin B has a structure expressed by the following Structural Formula (2).

Figure 2:
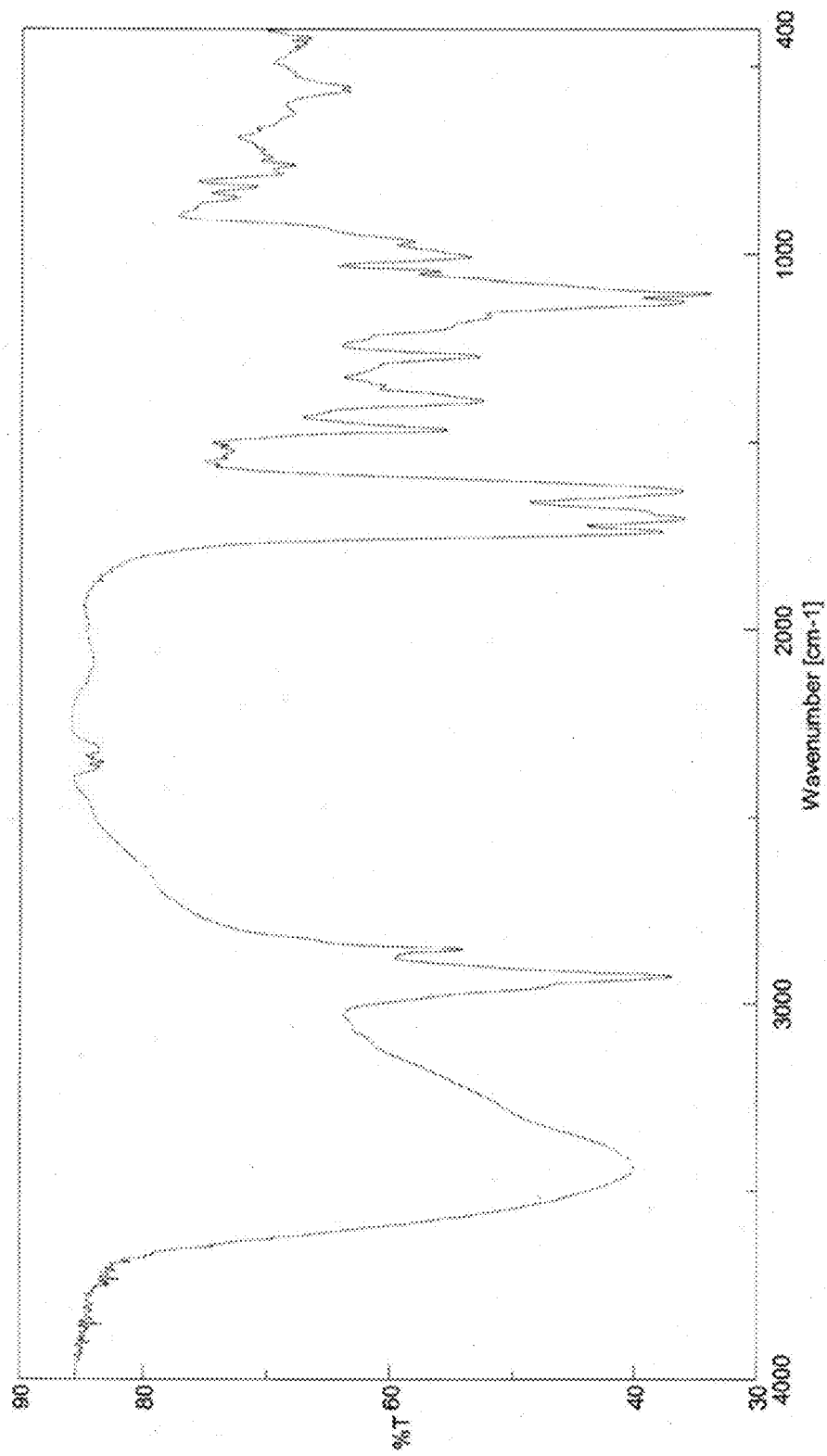
FIG. 2 is a chart of an infrared absorption spectrum of a compound expressed by Structural Formula (2) measured by a KBr tablet method.
Figure 3:
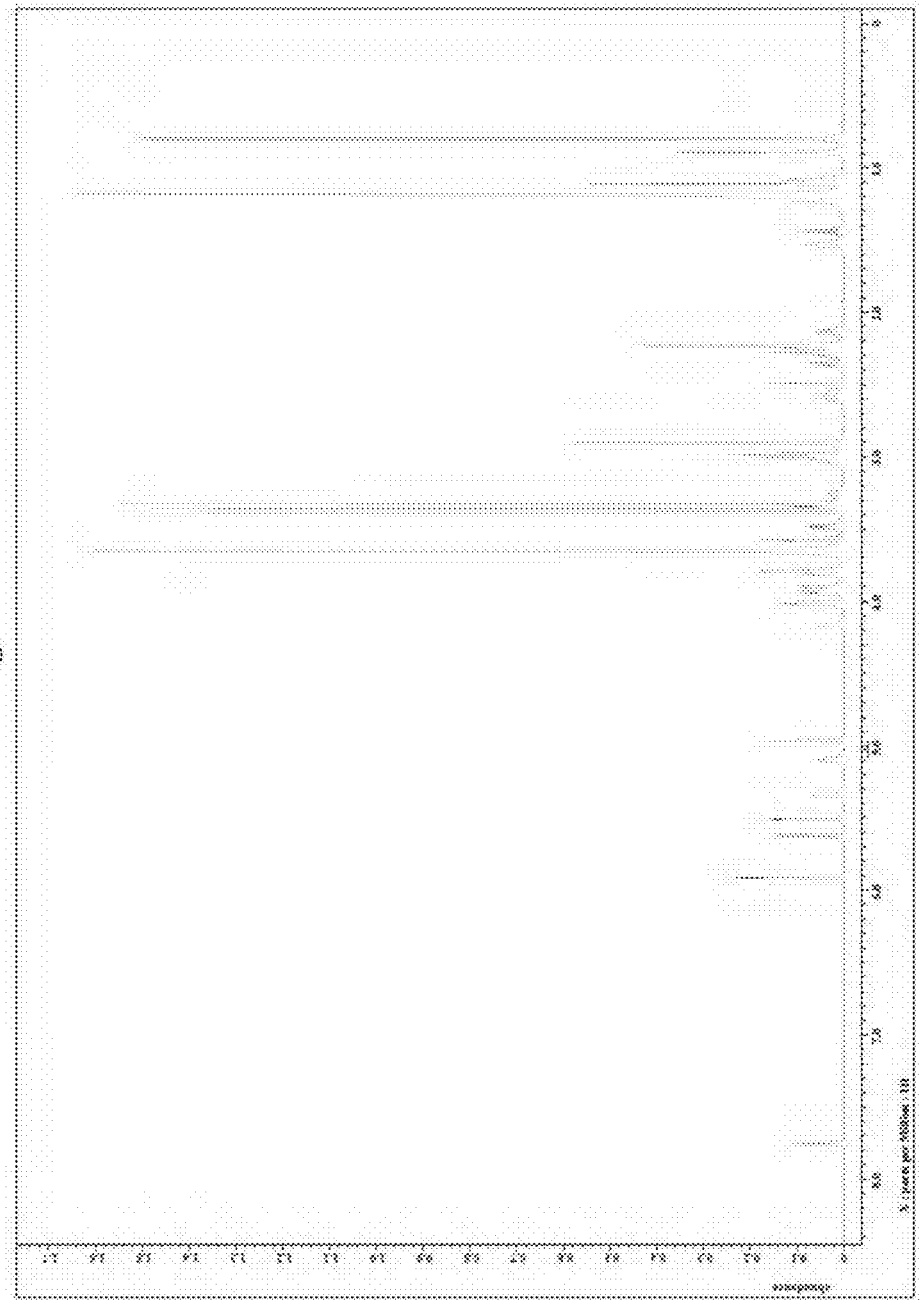
FIG. 3 is a chart of a proton nuclear magnetic resonance spectrum of a compound expressed by Structural Formula (2).

(1) Appearance: Colorless powder
(2) Molecular formula: $C_{53}H_{87}N_5O_{22}$
(3) High resolution mass spectrometry (HRFABMS: negative ion mode):
    Found: 1144.5750 $(M-H)^-$
    Calcd: 1144.5764
(4) Specific rotation: $[\alpha]_D^{23}$ $-2.6°$ (c 0.91, DMSO)
(5) UV absorption spectrum (in methanol):
    A UV absorption spectrum measured in methanol solution is as follows.
    $\lambda_{max}$ nm ($\epsilon$): 261 (8,000)
    The UV absorption spectrum is shown in FIG. 1.
(6) Infrared absorption spectrum:
    An infrared absorption spectrum measured by a KBr tablet method is shown in FIG. 2.
(7) Proton nuclear magnetic resonance spectrum:
    A proton NMR spectrum measured at room temperature and 600 MHz in a solvent mixture of deuterated dimethyl sulfoxide:deuterated water (=10:1) is shown in FIG. 3.

Figure 4:
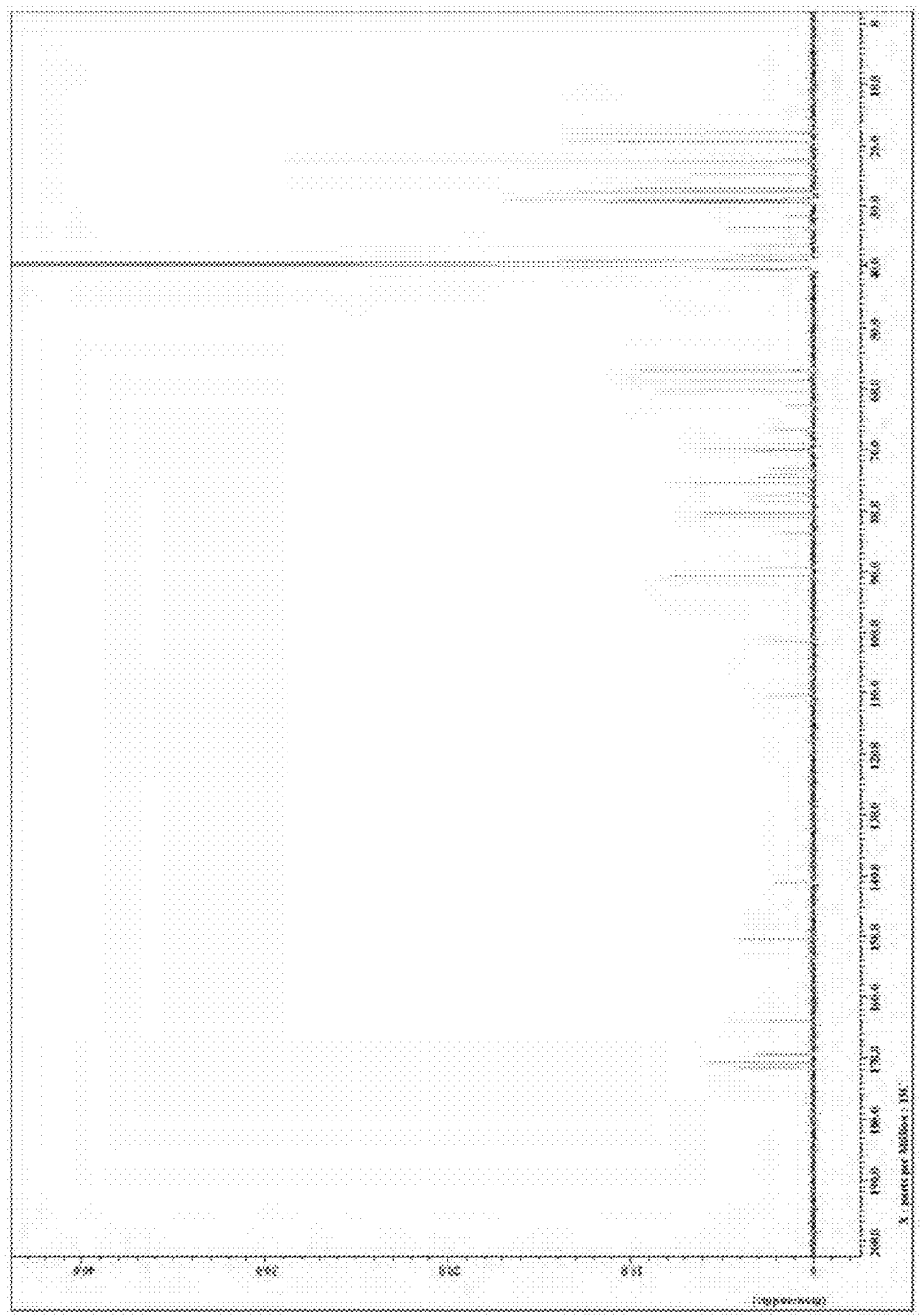
FIG. 4 is a chart of a $^{13}C$ nuclear magnetic resonance spectrum of a compound expressed by Structural Formula (2).

(8) $^{13}C$ nuclear magnetic resonance spectrum:

A $^{13}C$ NMR spectrum measured at room temperature and 150 MHz in a solvent mixture of deuterated dimethyl sulfoxide:deuterated water (=10:1) is shown in FIG. 4.

(9) Solubility:
    It is soluble in methanol, DMSO and water, but is insoluble in ethyl acetate.

(10) TLC:
    Through thin-layer chromatography using silica gel 60F$_{254}$ (product of Merck Co.) and a developing solvent of butanol:methanol:water (4:1:2), the Rf value is 0.44.

Structural Formula (2)

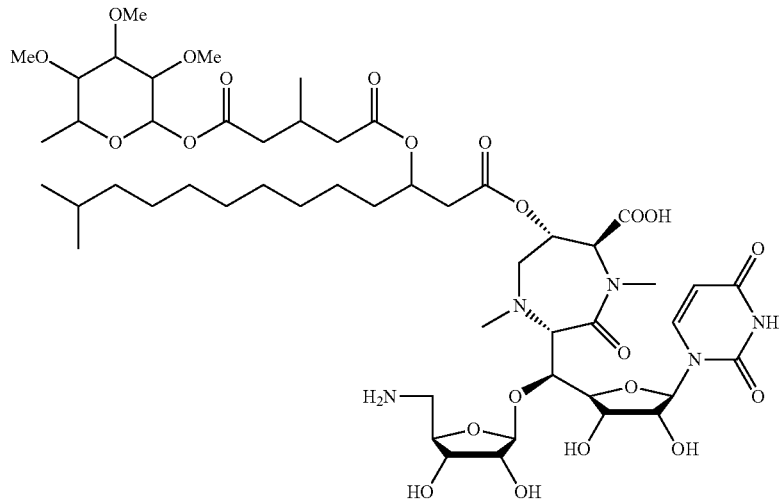

In Structural Formula (2), "Me" is a methyl group.

Production Example 2

<Production of Compound Expressed by Structural Formula (1)>

The compound expressed by the Structural Formula (1) (CPZEN-45) was produced in the same manner as in Example 1 of JP-A No. 2010-83847 as CPZEN-45 trifluoroacetate in the form of colorless crystals.

—Physico-Chemical Properties of CPZEN-45—

Physico-chemical properties of CPZEN-45 trifluoroacetate are as follows, confirming that CPZEN-45 has a structure expressed by the following Structural Formula (1).

Figure 5:
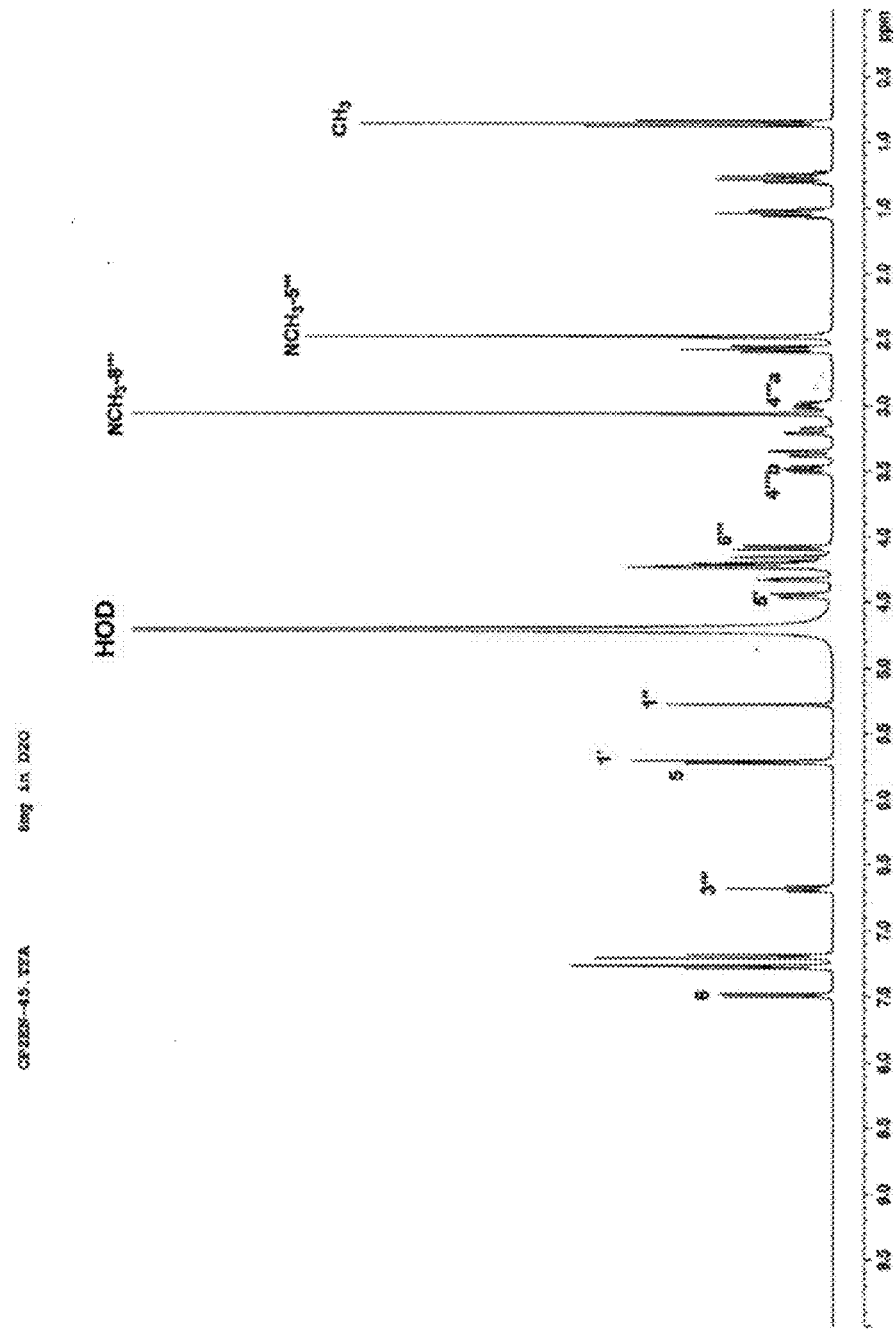
FIG. 5 is a chart of a proton nuclear magnetic resonance spectrum of a compound expressed by Structural Formula (1).
Figure 6:
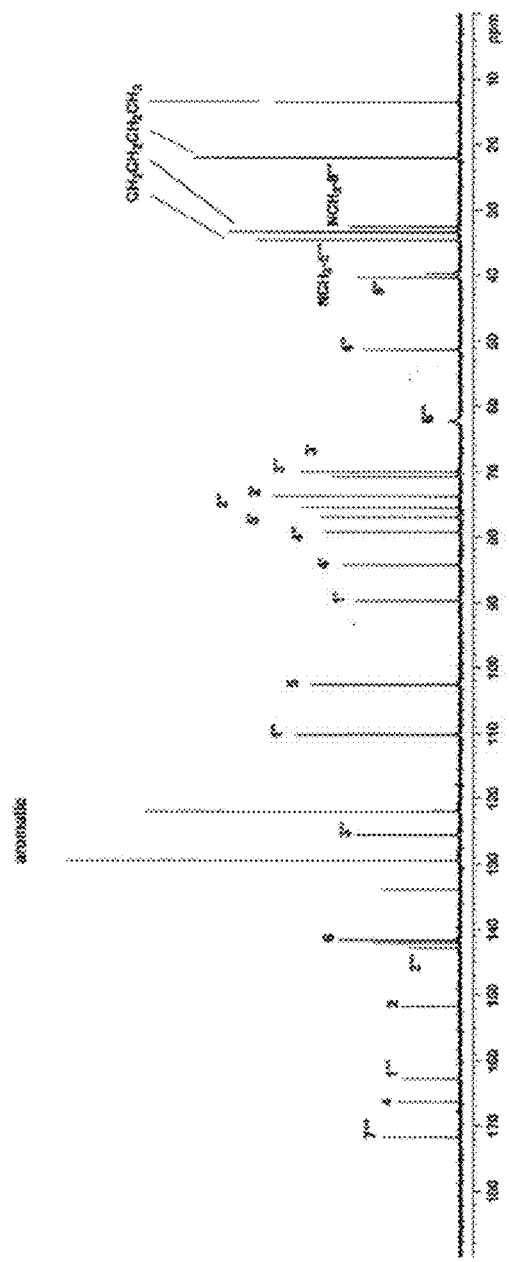
FIG. 6 is a chart of a $^{13}C$ nuclear magnetic resonance spectrum of a compound expressed by Structural Formula (1).

(1) Melting point: 175° C.-177° C. (decomposition)
(2) Specific rotation: $[\alpha]_D^{22}$ $+79°$ (c1, MeOH)
(3) Mass spectrum (ESI-MS):
    m/z 801 $[M+CF_3COOH-H]^-$
(4) $^{19}F$-NMR spectrum (376.5 MHz, in deuterated DMSO, Freon 11 internal standard): $\delta$-73.86 (s, $CF_3$)
(5) Proton nuclear magnetic resonance spectrum (500 MHz, in deuterated water, TMS internal standard):
    A proton nuclear magnetic resonance spectrum is shown in FIG. 5.
(6) $^{13}C$ nuclear magnetic resonance spectrum (126.8 MHz, in deuterated water, TMS internal standard):
    A $^{13}C$ nuclear magnetic resonance spectrum is shown in FIG. 6.

Structural Formula (1)

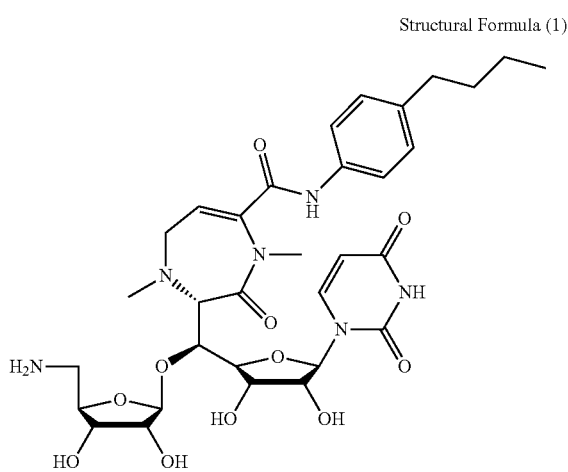

Test Example 1: Comparison Between CPZEN-45 and Caprazamycin B in Terms of Antibacterial Activity Antibacterial effects of caprazamycin B and CPZEN-45 against various bacteria were tested by measuring their MICs. The results are shown in Table 1.

<Measurement of MIC (Minimum Inhibitory Concentration)>

—Mycobacteria—

The MIC for Mycobacteria was measured by an agar dilution method. Specifically, bacterial cells were inoculated in media containing the drug 2-fold serially diluted (7H10 agar media containing glycerol and OADC). The bacterial cells were cultured at 37° C. for 2 days to 14 days and measured for MIC.

—Microorganisms Other than Mycobacteria—

The MICs for microorganisms other than Mycobacteria were measured by an agar dilution method. Specifically, bacterial cells were inoculated in media containing the drug 2-fold serially diluted (Mueller-Hinton agar media). The bacterial cells were cultured at 37° C. for 18 hours and measured for MIC.

Also, CPZEN-45 showed no antibacterial activity against Staphylococcus aureus FDA209 strain and Staph. aureus MRSA No. 5 strain in which WecA or an ortholog thereof is not essential for their growth, nor Streptococcus pneumoniae S-223 strain and Str. pneumoniae CR-2 strain which do not have WecA or an ortholog thereof.

Test Example 2: Synthesis of Polymers in B. subtilis 168 Strain

In the following manner, B. subtilis 168 strain (obtained from ATCC), which is Bacillus subtilis showing susceptibility to CPZEN-45 and caprazamycin B similar to that shown by tuberculosis bacteria, was used to test the synthesis of polymers in the presence of drug solutions containing the following drugs.

<Drug>
CPZEN-45 (produced in Production Example 2)
Caprazamycin B (produced in Production Example 1)
Tunicamycin
Vancomycin
Levofloxacin <Test Method>

Cells of B. subtilis 168 strain were cultured in a nutrient broth (NB medium) at 37° C. and 140 spm of shaking speed until logarithmic growth phase (OD600=0.2) to prepare a bacterial culture.

Each (0.01 mL) of the drug solutions 2-fold serially diluted and the bacterial culture (0.09 ml) were added to a 96-well plate, followed by mixing and statically culturing at 37° C. for 5 minutes.

After culturing, 0.01 mL of each radioactively labeled compound prepared to have the following concentration (hereinafter may be referred to as a "radioactive-labelled compound") was added to the wells, followed by statically culturing at 37° C. for 10 minutes.

Thereafter, 0.1 mL of 10% aqueous trichloroacetic acid solution was added to the wells to insolubilize polymer components of bacterial. Next, the culture was transferred to a 96-well plate equipped with a filter. After the liquid had been filtered off, 0.2 mL of 5% aqueous trichloroacetic acid solution was used to wash the filter three times.

TABLE 1

| Strain | MIC (μg/mL) Caprazamycin B | MIC (μg/mL) CPZEN-45 | Supplier or other information |
|---|---|---|---|
| Mycobacterium tuberculosis H37Rv | 3.13 | 1.56 | ATCC |
| Mycobacterium bovis BCG | 4 | 2 | National Institute of Infectious Diseases |
| Bacillus subtilis PCI219 | 3.13 | 1.56 | Strain equivalent to ATCC6633 strain |
| Bacillus subtilis 168 | 4 | 4 | ATCC |
| Staphylococcus aureus FDA209P | 1.56 | 12.5 | SRL Co., Ltd. |
| Staph. aureus MRSA No. 5 | 1.56 | 100 | Meiji Seika |
| Enterococcus faecalis JCM 5803 | 6.25 | 8 | JCM |
| Ent. faecalis NCTC12203 (VRE) | 12.5 | 8 | NCTC |
| Streptococcus pneumoniae S-223 | 0.78 | 16 | Kitasato University |
| Str. pneumoniae CR-2 | 6.25 | 128 | Kitasato University |
| Escherichia coli K-12 | >100 | >100 | ATCC |

As shown in Table 1, difference was found between caprazamycin B and CPZEN-45 in terms of antibacterial activity against, for example, Staphylococcus aureus FDA209P, which presumably indicates that they have different action mechanisms for antibacterial activity.

After drying, radioactivity remaining on the filter was measured with a liquid scintillation counter (TRI-CARB 2800TR, product of PerkinElmer, Inc.) to evaluate the amount of polymers synthesized by the bacterial cells. The results are shown in FIGS. 7A to 7E.

—Radioactive-Labeled Compound—
- 0.1 μCi/μL N-acetyl-D-[1-$^{14}$C]glucosamine (used for evaluating the synthesis of peptidoglycan, hereinafter may be referred to as "N-acetyl-D-glucosamine")
- 0.01 μCi/μL [$^{14}$C(U)]glycerol (used for evaluating the synthesis of teichoic acid, hereinafter may be referred to as "Glycerol")
- 1 μCi/μL [1-$^{14}$C]acetate (used for evaluating the synthesis of fatty acids of cell membrane, hereinafter may be referred to as "Acetic acid")
- 1 μCi/μL [methyl-$^{3}$H]thymidine (used for evaluating the synthesis of DNA synthesis, hereinafter may be referred to as "Thymidine")
- 1 μCi/μL [5,6-$^{3}$H]uridine (used for evaluating the synthesis of RNA synthesis, hereinafter may be referred to as "Uridine")
- 5 μCi/μL L-[4,5-$^{3}$H]leucine (used for evaluating the synthesis of protein synthesis, hereinafter may be referred to as "Leucine")

Figure 7A:
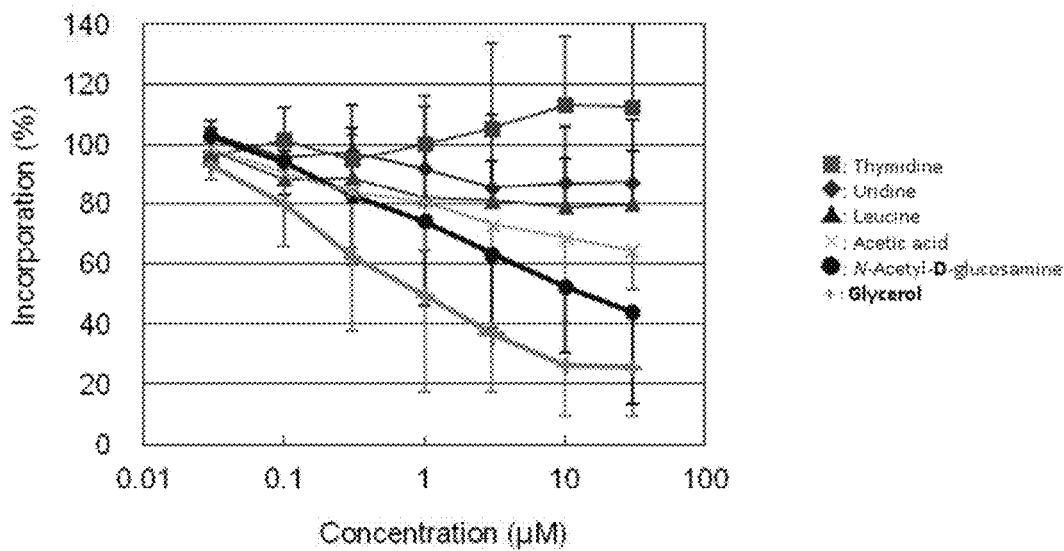
FIG. 7A is a graph of results obtained when CPZEN-45 is used as a drug in Test Example 2.
Figure 7B:
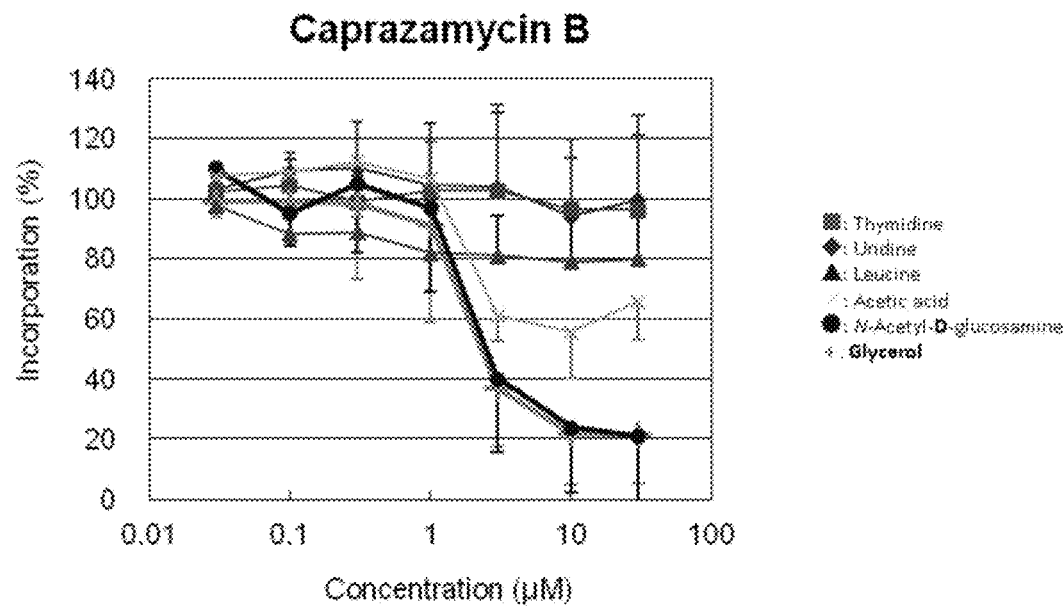
FIG. 7B is a graph of results obtained when caprazamycin B is used as a drug in Test Example 2.
Figure 7C:
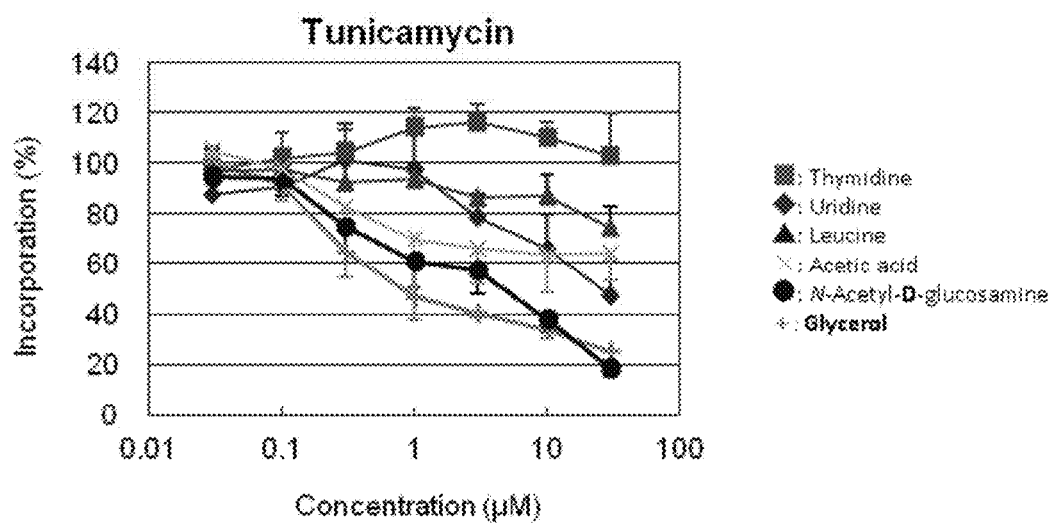
FIG. 7C is a graph of results obtained when tunicamycin is used as a drug in Test Example 2.
Figure 7D:
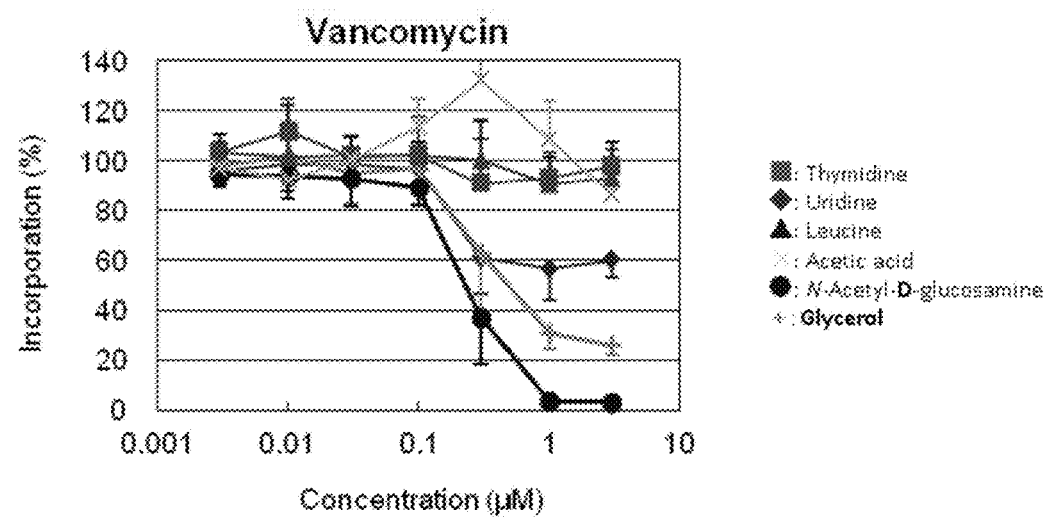
FIG. 7D is a graph of results obtained when vancomycin is used as a drug in Test Example 2.
Figure 7E:
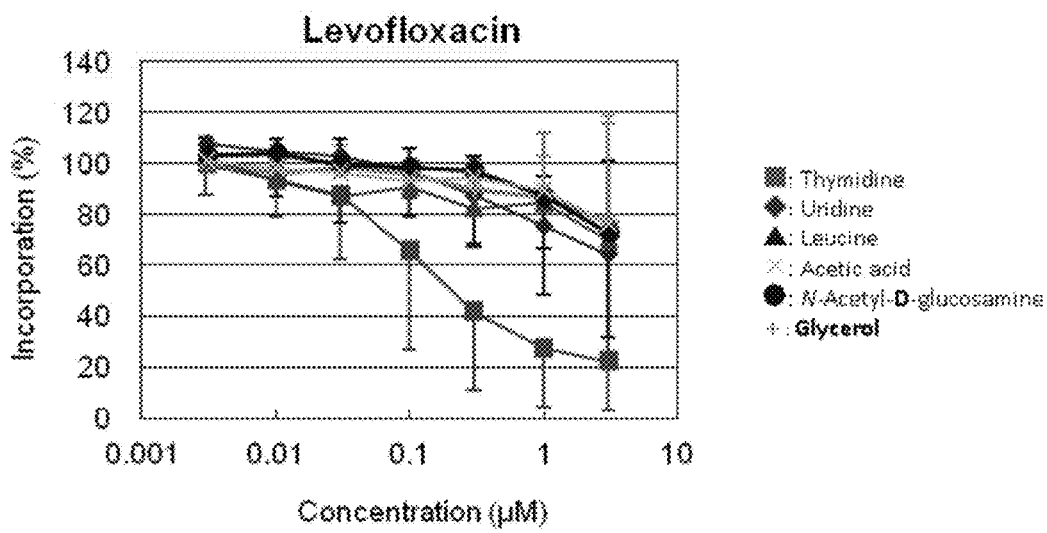
FIG. 7E is a graph of results obtained when levofloxacin is used as a drug in Test Example 2.

FIG. 7A shows results obtained when the drug was CPZEN-45, FIG. 7B shows results obtained when the drug was caprazamycin B, FIG. 7C shows results obtained when the drug was tunicamycin, FIG. 7D shows results obtained when the drug was vancomycin, and FIG. 7E shows results obtained when the drug was levofloxacin. In FIGS. 7A to 7E, "filled square" denotes incorporation of the [methyl-$^{3}$H] thymidine, "filled rhomboid" denotes incorporation of the [5,6-$^{3}$H]uridine, "filled triangle" denotes incorporation of the L-[4,5-$^{3}$H]leucine, "x-mark" denotes incorporation of the [1-$^{14}$C]acetate, "filled circle" denotes incorporation of the N-acetyl-D-[1-$^{14}$C]glucosamine, and "+-mark" denotes incorporation of the [$^{14}$C(U)]glycerol.

As shown in FIG. 7A, it was confirmed that incorporation into bacterial cells of glycerol, a constituent component of teichoic acid which is one main constituent component of a cell wall, was inhibited in the presence of CPZEN-45.

This was the same result as tunicamycin known to inhibit TagO (an ortholog of WecA) in *B. subtilis* as shown in FIG. 7C.

Also, as shown in FIG. 7B, it was confirmed that incorporation into bacterial cells of N-acetyl-D-glucosamine which is a constituent component of peptidoglycan in the presence of caprazamycin B inhibiting MraY (an ortholog of MurX) in *B. subtilis*.

This was the same result as vancomycin having similar inhibitory activity as shown in FIG. 7D.

Note that, as shown in FIG. 7E, levofloxacin which inhibits DNA synthesis gave different results from CPZEN-45, caprazamycin B, tunicamycin, and vancomycin.

Teat Example 3-1: Preparation of Drug-Resistant Bacteria and Identification of Genotype

*B. subtilis* 168 strain (obtained from ATCC) was used as a parent strain to prepare bacteria having resistance to caprazamycin B or CPZEN-45 in the following manner, and their genotype was confirmed.
<Preparation of Resistant Bacteria>
*B. subtilis* 168 strain was used as a parent strain.

Cells of the *B. subtilis* 168 strain were inoculated so as to have a final concentration of 1% in a nutrient broth (NB medium) containing a drug (caprazamycin B or CPZEN-45) at a concentration 1/8 times to 4 times the MIC, followed by statically culturing at 37° C. and 141 spm for 24 hours.

The culture of bacteria having grown in the presence of the drug at a concentration 1/4 times the MIC was used as an inoculation source to perform culturing under the same conditions again.

This procedure was repeated until the MIC exceeded 128 times that of the parent strain to prepare resistant bacteria.
—Measurement of MIC (Minimum Inhibitory Concentration)—

The MIC was measured by a microbroth dilution method. Specifically, an LB broth (LB medium) was used as a medium. Each solution (0.1 mL) containing a drug 2-fold serially diluted and the bacterial culture (0.1 mL) were added to a 96-well plate, followed by mixing. The bacteria were cultured at 37° C. for 16 hours and measured for MIC.

Note that, the MIC was also measured for tunicamycin and vancomycin. The results are shown in Table 2.
—Identification of Genotype—

The genotypes of mraY gene and tagO gene of the parent strain and the resistant bacteria were identified in the following manner. The results are shown in Table 2.

PCR was performed using the genome DNA of the parent strain and the resistant bacteria as a template to amplify fragments of mraY gene and tagO gene. Then, the fragments of both the genes were obtained by agarose gel electrophoresis. The sequences of the obtained gene fragments were identified with a DNA sequencer (ABI3730, product of Applied Biosystems, Inc.).

The sequences of primers used for the amplification of mraY gene are as follows.

```
5'-terminal side:
                            (SEQ ID NO: 9)
5'-AGGACATGAAACCTATCAGCAG-3'

3'-terminal side:
                            (SEQ ID NO: 10)
5'-TCTCCGCAAACAACTTCGATTC-3'
```

The sequences of primers used for the amplification of tagO gene are as follows.

```
5'-terminal side:
                            (SEQ ID NO: 11)
5'-CCGGACACAAGATTGGAATTGC-3'

3'-terminal side:
                            (SEQ ID NO: 12)
5'-AGCAGCACAAGCTCAAACAAC-3'
```

TABLE 2

| B. subtilis strains | MIC (μg/ml) | | | | Genotype | |
| --- | --- | --- | --- | --- | --- | --- |
| | CPZB | CPZEN-45 | TUN | VCM | mraY | tagO |
| 168 (parent strain) | 4 | 4 | 0.25 | 0.25 | WT | WT |
| CPZB-resistant strain | >128 | 4 | 4 | 0.25 | WT | WT |
| CPZEN-45-resistant strain | 4 | >128 | 1 | 0.5 | WT | T728G (Ile243Ser) |

In Table 2, "168" denotes the parent strain, "CPZB" denotes caprazamycin B, "TUN" denotes tunicamycin, "VCM" denotes vancomycin, and "WT" denotes wild type.

From Table 2, it was confirmed in the case of the CPZEN-45-resistant strain that there was a strain having mutation in tagO which is a gene encoding TagO, suggesting that CPZEN-45 targets TagO.

Test Example 3-2

Study on Target Gene

A strain highly expressing mraY gene or tagO gene was prepared in the following manner, and the MIC of the strain was measured.

<Preparation of Strain Highly Expressing mraY Gene or tagO Gene>

Figure 8:
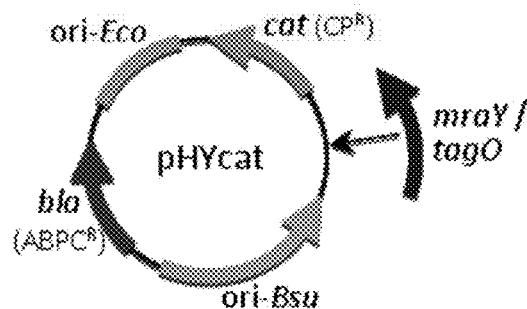
FIG. 8 outlines pHYcat.

Commercially available plasmids pHY300PLK (product of TAKARA BIO INC.) and pHT01 (product of German MoBiTec, GmbH) were used to produce plasmid "pHYcat" capable of replicating in *Bacillus subtilis*. The outline of the pHYcat is shown in FIG. 8.

The plasmid "pHYcat" was obtained as follows. Specifically, both of the pHY300PLK and the pHT01 were treated with restriction enzymes BanI and PvuII, and the resultant 2,848-bp DNA fragment of the pHY300PLK and the resultant 2,149-bp DNA fragment of the pHT01 were ligated with each other.

The "pHYcat" was treated with restriction enzyme NheI and its ends were blunted with a mung bean nuclease. Into the obtained fragment was inserted mraY gene or tagO gene which had been amplified by PCR using the genome DNA of *B. subtilis* 168 strain as a template under the same conditions as those for the above identification of genotype. Through the above procedure, plasmids "pHYcat-mraY" and "pHYcat-tagO" were produced.

The "pHYcat-mraY" or "pHYcat-tagO" was introduced into the *B. subtilis* 168 strain to prepare an mraY highly expressing stain (hereinafter may be referred to as "168/pHYcat-mraY strain") and a tagO highly expressing strain (hereinafter may be referred to as "168/pHYcat-tagO strain"). Also, the pHYcat was introduced into *B. subtilis* 168 strain to prepare a control strain.

—Measurement of MIC (Minimum Inhibitory Concentration)—

The above-prepared 3 strains were used to measure MICs in the same manner as in Test Example 3-1. The results are shown in Table 3.

TABLE 3

| *B. subtilis* strains | MIC (μg/ml) | | | |
| --- | --- | --- | --- | --- |
| | CPZB | CPZEN-45 | TUN | VCM |
| 168/pHYcatA | 4 | 8 | 1 | 0.5 |
| 168/pHYcat-mraY | >128 | 8 | 1 | 0.5 |
| 168/pHYcat-tagO | 4 | 64 | 16 | 1 |

In Table 3, "168/pHYcatA" denotes a strain to which "pHYcat" was introduced. "168/pHYcat-mraY" denotes a strain to which "pHYcat-mraY" was introduced, "168/pHYcat-tagO" denotes a strain to which "pHYcat-tagO" was introduced, "CPZB" denotes caprazamycin B, "TUN" denotes tunicamycin, and "VCM" denotes vancomycin.

From Table 3, it was confirmed that the mraY highly expressing stain had resistance to caprazamycin B but did not have resistance to CPZEN-45. It was also confirmed that the tagO highly expressing stain did not have resistance to caprazamycin B but did have resistance to CPZEN-45. In addition, tagO highly expressing stain was confirmed to have resistance to tunicamycin known to inhibit enzymatic activity of TagO. The results of Test Example 3-2 also suggest that CPZEN-45 targets TagO.

The above results are thought to be consistent with the fact in Test Example 1 that CPZEN-45 showed no antibacterial activity against *Staphylococcus aureus* FDA209 strain and *Staph. aureus* MRSA No. 5 strain in which WecA or an ortholog thereof is not essential for their growth, nor *Streptococcus pneumoniae* S-223 strain and *Str. pneumoniae* CR-2 strain which do not have WecA or an ortholog thereof.

Test Example 4: Evaluation of Enzymatic Activity

The activities of enzymes MraY and TagO were measured in the following manner using disruption liquids of bacterial cells of the 168/pHYcat-mraY strain and the 168/pHYcat-tagO highly expressing these enzymes and produced in Test Example 3-2.

As a control, tunicamycin, vancomycin and levofloxacin were tested similarly.

<Preparation of Enzyme Liquid>

The bacterial cells were cultured in an LB medium until logarithmic growth phase (OD600=0.4) and then collected through centrifuging (5,000 rpm, 10 min), followed by washing twice with a TMS buffer (50 mM Tris-HCl (pH 7.5), 625 mM sucrose, 10 mM $MgCl_2$, 5 mM 3-mercapto-1,2-propanediol, 1 mM PMSF).

Next, the precipitate was re-suspended in a TMS buffer having a volume 1/40 the initial volume, and the bacterial cells were disrupted through probe sonication (where the following procedure was repeated 10 times on ice: disrupting them for 30 sec and leaving them stand still for 30 sec). Then, undisrupted bacterial cells were removed through centrifuging (3,000 rpm, 10 min) and the supernatant was used as an enzyme liquid.

—Measurement of TagO Activity—

The TagO activity was measured by allowing 0.02 mL of the following reaction mixture to react at 30° C. for 1 hour.

After reaction, 0.2 mL of chloroform-methanol (2:1) solution was added to the reaction mixture to terminate the reaction, followed by centrifuging (15,000 rpm, 3 min).

Figure 9A:
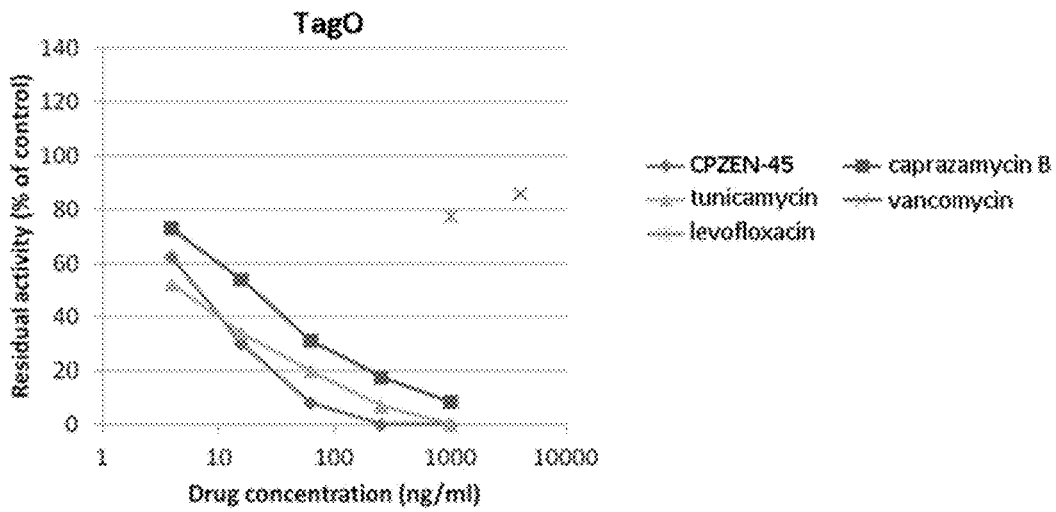
FIG. 9A is a graph of results obtained by evaluating enzymatic activity of TagO in Test Example 4.

Next, the lower layer containing the reaction product was analyzed through thin-layer chromatography (TLC, using as a developing solvent chloroform:methanol:water:concentrated aqueous ammonia=65:35:4:4) and autoradiography, to thereby calculate the enzymatic activity of TagO as a rate with respect to that of the control. The results are shown in FIG. 9A.

——Reaction Mixture——

Enzyme liquid: 250 ng total protein/μL

125 μM undecaprenyl phosphate

20 μM UDP-GlcNAc 0.05 μCi/μL UDP-GlcNAc, [glucosamine-6-$^3$H]-

100 mM Tris-HC 0.20 mM $MgCl_2$

1% CHAPS

—Measurement of MraY Activity—

The MraY activity was measured by allowing 0.02 mL of the following reaction mixture to react at 30° C. for 20 min.

After reaction, 0.02 mL of a reaction terminating liquid (butanol:a solution of pyridine in glacial acetic acid (final concentration: 6M)=2:1 (by volume)) was added to the reaction mixture to terminate the reaction, followed by centrifuging (15,000 rpm, 3 min).

Next, the lower layer containing the reaction product was analyzed through thin-layer chromatography (TLC, using as a developing solvent chloroform:methanol:water:concentrated aqueous ammonia=88:48:4:1) and autoradiography, to thereby calculate the enzymatic activity of MraY as a rate with respect to that of the control. The results are shown in FIG. 9B.

——Reaction Mixture——
Enzyme liquid: 20 ng total protein/μL
0.50 μM undecaprenyl phosphate
0.02 μCi/μL undecaprenyl phosphate, [1-$^3$H]-
50 μM UDP-MurNAc-pentapeptide
100 mM Tris-HCl
20 mM MgCl$_2$
10 mM Triton X-100

Figure 9B:
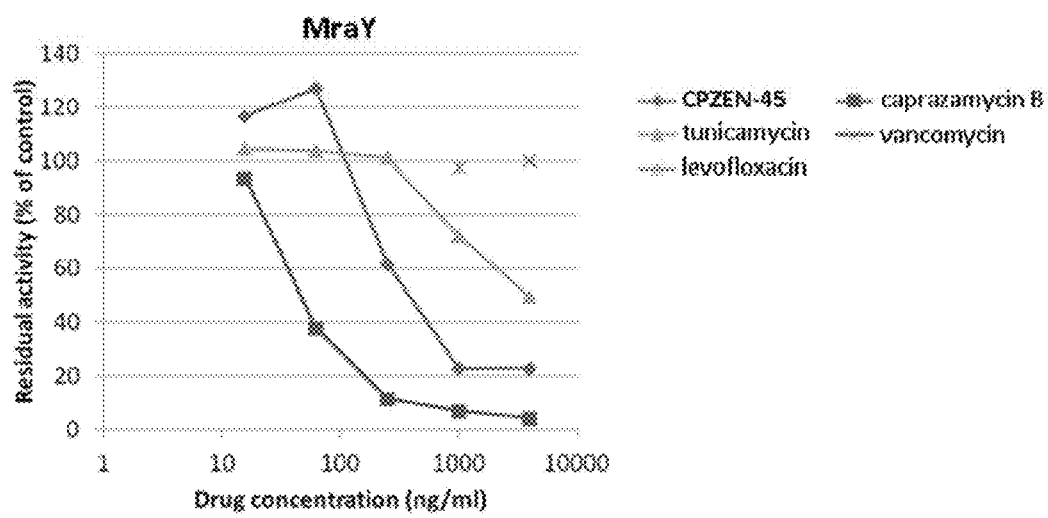
FIG. 9B is a graph of results obtained by evaluating enzymatic activity of MraY in Test Example 4.

In FIGS. 9A and 9B, "filled rhomboid" denotes the results of CPZEN-45, "filled square" denotes the results of caprazamycin B, "filled triangle" denotes the results of tunicamycin, "x-mark" denotes the results of vancomycin, and "*" denotes the results of levofloxacin.

The results of FIGS. 9A and 9B indicate that the enzymatic activity of TagO was inhibited by CPZEN-45 the most strongly, and the enzymatic activity of MraY was inhibited caprazamycin B the most strongly. Therefore, the results of Test Example 4 also suggest that CPZEN-45 targets TagO.

Test Example 5: Inhibitory Activity of CPZEN-45 Against WecA of *Mycobacterium smegmatis*

The inhibitory activity of CPZEN-45 against WecA of *Mycobacterium smegmatis*, which is closely related to tuberculosis bacteria, was tested in the following manner.

<Preparation of Enzyme Liquid>
Cells of *M. smegmatis* mc$^2$ 155 strain (obtained from ATCC) were cultured in a glycerol-alanine medium until logarithmic growth phase. The bacterial cells (10 g) were suspended in 30 mL of an A buffer. Using an ultrasonic disruptor (Soniprep 150; MSE Ltd., Crawley, Sussex, United Kingdom; 1 cm probe), the suspension was subjected to the following procedure on ice 10 times: disrupting them for 60 sec and leaving them stand still for 90 sec. After the disruption liquid of the bacterial cells had been centrifuged at 4° C. and 27,000 g for 12 min, the supernatant was further centrifuged at 4° C. and 100,000 g for 60 min to obtain a cell membrane fraction containing WecA. The cell membrane fraction was re-suspended in an appropriate amount of an A buffer, and the suspension was used as an enzyme liquid.

—Glycerol-Alanine Medium—
Glycerol (20 mL), BACTO CASITONE (product of Difco Co., Ltd.) (0.3 g), ammonium iron(III) citrate (0.05 g), dipotassium hydrogenphosphate (4.0 g), citric acid (2.0 g), L-alanine (1.0 g), magnesium chloride hexahydrate (1.2 g), potassium sulfate (0.6 g), ammonium chloride (2.0 g), Tween80 (0.2 g) and Antifoam A (product of Dow Corning, Co., Ltd.) (0.05 g) were dissolved in deionized water (1 L), and the solution was adjusted to 6.6 in pH with NaOH.

—A Buffer—
50 mM MOPS (adjusted to 8.0 in pH with KOH), 5 mM 2-mercaptoethanol, 10 mM MgCl$_2$ <Measurement of Enzymatic Activity of WecA>
A predetermined amount of CPZEN-45 was added to the following enzyme reaction mixture (liquid amount: 0.1 mL) and the resultant mixture was left to stand still at 37° C. for 1 hour for enzymatic reaction. Next, 1 mL of chloroform-methanol (2:1) solution was added to the reaction mixture to terminate the reaction. The mixture was vigorously stirred to extract the reaction product in the organic layer. An appropriate amount of the reaction product was subjected to thin-layer chromatography (TLC) and detected through autoradiography. The results are shown in FIG. 10.

Figure 10:
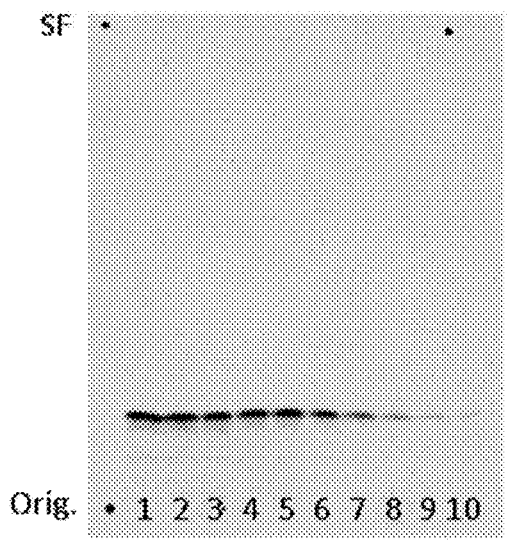
FIG. 10 illustrates results obtained in Test Example 5.

—Enzyme Reaction Mixture—
A mixture containing the above-prepared enzyme liquid (in an amount corresponding to 1 mg of the protein), ATP (60 μl) and [$^{14}$C]-UDP-GlcNAc 0.01 μCi/μL (0.1 mL) in the above A buffer In FIG. 10, "1" to "10" correspond sequentially to the results obtained when the amount of CPZEN-45 added was 0 μg/mL, 0.00019125 μg/mL, 0.0003825 μg/mL, 0.000765 μg/mL, 0.00153 μg/mL, 0.00306 μg/mL, 0.00611 μg/mL, 0.01221 μg/mL, 0.02441 μg/mL and 0.048828 μg/mL. "SF" denotes the upper end of the developing solvent and "Orig." denotes an original point.

As a result of quantification of an autoradiograph, the IC$_{50}$ was calculated as 0.0044 μg/mL, confirming that CPZEN-45 inhibits WecA of *Mycobacterium smegmatis* which is closely related to tuberculosis bacteria.

Table 4 shows homology among the amino acid sequences of TagO of *B. subilis*, WecA of *M. smegmatis*, and WecA of *M. tuberculosis*. TagO of *B. subilis* and WecA of *M. smegmatis* are enzymes that catalyze the same reaction. Also, as described in Table 4, TagO of *B. subilis* and WecA of *M. tuberculosis* have a homology of 35.7%, and WecA of *M. smegmatis* and WecA of *M. tuberculosis* have a homology of 86.0%. Furthermore, in these enzymes, essential amino acid sequences for enzyme reaction are well preserved. That is, these enzymes are orthologs to each other.

Therefore, it is thought that CPZEN-45 shows its antibacterial effect by targeting WecA or an ortholog thereof of tuberculosis bacteria.

TABLE 4

| | | | |
|---|---|---|---|
| WecA of *M. tuberculosis* | 100% | | |
| WecA of *M. smegmatis* | 86.0% | 100% | |
| TagO of *B. subtilis* | 35.7% | 35.9% | 100% |
| | WecA of *M. tuberculosis* | WecA of *M. smegmatis* | TagO of *B. subtilis* |

Figure 11A:
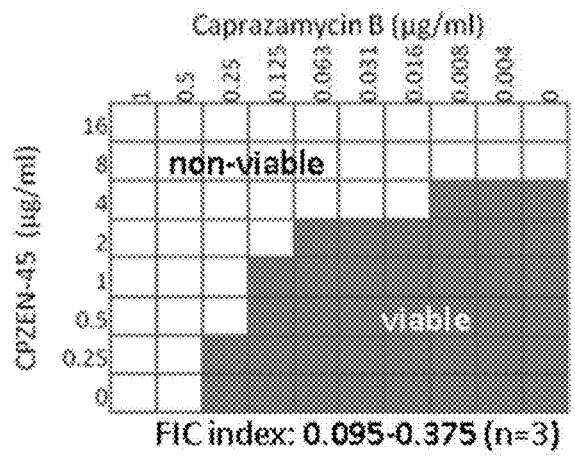
FIG. 11A illustrates results obtained when CPZEN-45 and caprazamycin B are used in combination in Test Example 6.
Figure 11B:
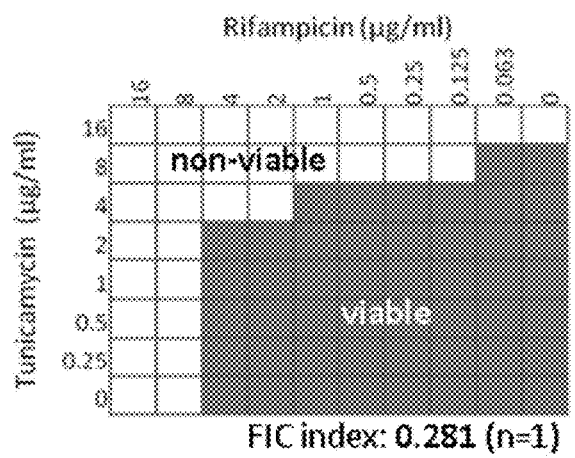
FIG. 11B illustrates results obtained when tunicamycin and rifampicin are used in combination in Test Example 6.
Figure 11C:
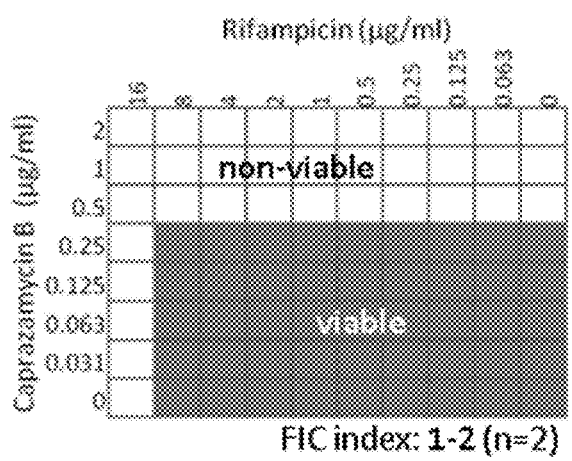
FIG. 11C illustrates results obtained when caprazamycin B and rifampicin are used in combination in Test Example 6.

Test Example 6: Synergistic Effects of the Inhibitor for WecA or an Ortholog Thereof, and at Last One of the Inhibitor for MurX or an Ortholog Thereof and the RNA Synthesis Inhibitor Whether the following combinations of drugs show synergistic effects against *M. smegmatis* 607 strain (obtained from ATCC) was tested by measuring a MIC and calculating a FIC index in the following manner. The results are shown in FIGS. 11A to 11C.

—Measurement of MIC (Minimum Inhibitory Concentration)—
The MIC was measured by a microbroth dilution method. Specifically, an OADC-containing 7H9 broth was used as a medium. Each solution (0.1 mL) containing one drug or two drugs 2-fold serially diluted and the bacterial culture (0.1 mL) were added to a 96-well plate, followed by mixing. The bacteria were cultured at 37° C. for 3 days and measured for MIC.

<Combination of Drugs (Drug A and Drug B)>
(1) Drug A: CPZEN-45 (the inhibitor for WecA or an ortholog thereof), Drug B: Caprazamycin B (the inhibitor for MurX or an ortholog thereof)
(2) Drug A: Tunicamycin (the inhibitor for WecA or an ortholog thereof), Drug B: Rifampicin (the RNA synthesis inhibitor)
(3) Drug A: Caprazamycin B (the inhibitor for MurX or an ortholog thereof), Drug B: Rifampicin (the RNA synthesis inhibitor)

<FIC Index (Fractional Inhibitory Concentration Index)>

The FIC index was calculated from the following equation (1).

FIC index=the minimum value of (FIC of Drug A+FIC of Drug B)  Equation (1)

FIC of Drug A=MIC of a combination of Drug A and Drug B/MIC of Drug A alone

FIC of Drug B=MIC of a combination of Drug A and Drug B/MIC of Drug B alone

It is possible to judge the effects of the combination of the drugs based on the FIC index.

FIC index≤0.5 . . . Synergetic 0.5<FIC index≤1 . . . Additive

1<FIC index≤2 . . . Indifferent

FIC index>2 . . . Antagonistic

FIG. 11A illustrates results obtained when CPZEN-45 and caprazamycin B were used in combination (vertical axis: CPZEN-45, horizontal axis: caprazamycin B), FIG. 11B illustrates results obtained when tunicamycin and rifampicin were used in combination (vertical axis: tunicamycin, horizontal axis: rifampicin), and FIG. 11C illustrates results obtained when caprazamycin B and rifampicin were used in combination (vertical axis: caprazamycin B, horizontal axis: rifampicin). Also, in FIGS. 11A to 11C, the colored portion indicates "viable" and the uncolored portion indicates "non-viable".

From FIGS. 11A to 11C, synergistic effects by combinational use were found in the combination of CPZEN-45 (the inhibitor for WecA or an ortholog thereof) and caprazamycin B (the inhibitor for MurX or an ortholog thereof (FIC index=0.095 to 0.375) and the combination of tunicamycin (the inhibitor for WecA or an ortholog thereof) and rifampicin (the RNA synthesis inhibitor) (FIC index=0.281). In contrast, no synergistic effect was found in the combination of caprazamycin B (the inhibitor for MurX or an ortholog thereof) and rifampicin (the RNA synthesis inhibitor) (FIC index=1 to 2).

As described above, it has been found that quite excellent effects against acid-fast bacillus can be obtained by using the inhibitor for WecA or an ortholog thereof in combination with at least one of the inhibitor for MurX or an ortholog thereof and the RNA synthesis inhibitor.

Accession Number

FERM BP-7218

Aspects of the present invention are, for example, as follows.

<1> A drug combination against acid-fast bacillus, including:

an inhibitor for WecA or an ortholog thereof, and at least one of an inhibitor for MurX or an ortholog thereof and an RNA synthesis inhibitor, wherein the inhibitor for WecA or an ortholog thereof is used in combination with the at least one of an inhibitor for MurX or an ortholog thereof and an RNA synthesis inhibitor.

<2> The drug combination against acid-fast bacillus according to <1>, wherein the inhibitor for WecA or an ortholog thereof contains a compound expressed by the following Structural Formula (1), and the inhibitor for MurX or an ortholog thereof contains a compound expressed by the following Structural Formula (2):

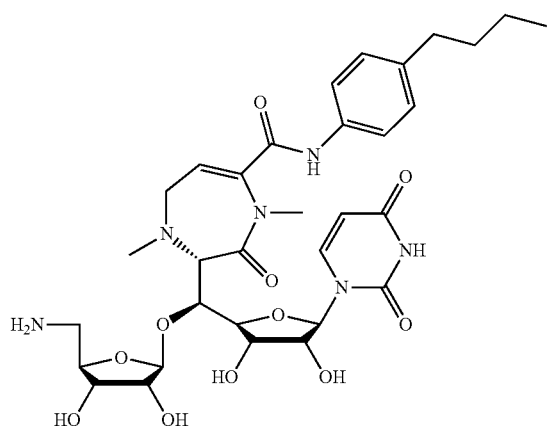

Structural Formula (1)

-continued

Structural Formula (2)

where in Structural Formula (2), "Me" is a methyl group.

<3> The drug combination against acid-fast bacillus according to <1>, wherein the inhibitor for WecA or an ortholog thereof contains tunicamycin, and the RNA synthesis inhibitor contains rifampicin.

<4> The drug combination against acid-fast bacillus according to any one of <1> to <3>, wherein the acid-fast bacillus is tuberculosis bacteria.

<5> A screening method for a drug against acid-fast bacillus, the method including:

measuring activity of a test substance against WecA or an ortholog thereof.

<6> The screening method for a drug against acid-fast bacillus according to <5>, wherein the acid-fast bacillus is tuberculosis bacteria.

<7> An inhibitor for WecA or an ortholog thereof, including:

a compound expressed by the following Structural Formula (1):

Structural Formula (1)

INDUSTRIAL APPLICABILITY

The drug combination against acid-fast bacillus of the present invention has excellent drug efficacy to acid-fast bacillus and can suitably be used for the treatment of patients infected with tuberculosis bacteria which raise a serious problem today.

The screening method of the present invention can provide a drug against acid-fast bacillus having excellent effects against acid-fast bacillus.

The inhibitor for WecA or an ortholog thereof of the present invention can suitably be used as an active ingredient of the drug against acid-fast bacillus and also as a reagent in the screening method of the present invention.

The invention claimed is:

1. A method for treating an individual infected with *Mycobacterium*, comprising: administering, to the individual, an inhibitor for WecA or an ortholog thereof and an inhibitor for MurX or an ortholog thereof, wherein the inhibitor for WecA or an ortholog thereof comprises a compound expressed by following Structural Formula (1) or a pharmacologically acceptable salt thereof, and the inhibitor for MurX or an ortholog thereof comprises a compound expressed by following Structural Formula (2) or a pharmacologically acceptable salt thereof:

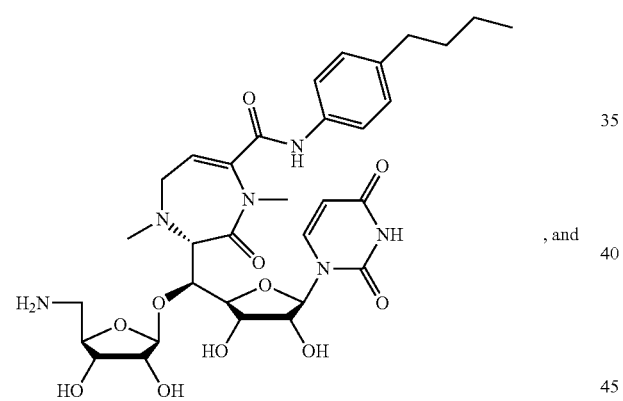

Structural Formula (1)

, and

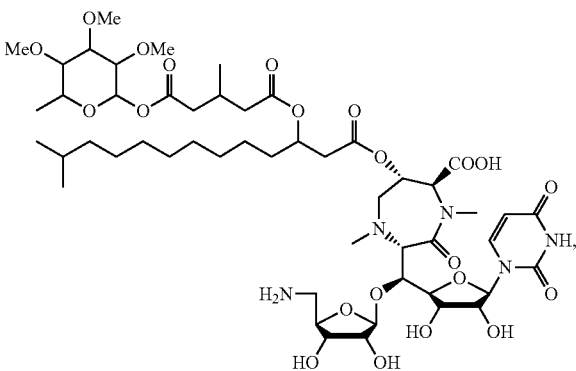

Structural Formula (2)

wherein the Structural Formula (2), Me is a methyl group.

2. The method according to claim 1, wherein the individual is at least one animal selected from the group consisting of humans, monkeys, pigs, bovines, sheep, goats, dogs, cats, mice, rats, and birds.

* * * * *

UNITED STATES PATENT AND TRADEMARK OFFICE
CERTIFICATE OF CORRECTION

PATENT NO. : 9,839,648 B2  
APPLICATION NO. : 14/895719  
DATED : December 12, 2017  
INVENTOR(S) : Ishizaki et al.

Page 1 of 3

It is certified that error appears in the above-identified patent and that said Letters Patent is hereby corrected as shown below:

In the Specification

Columns 13 and 14, Lines 18-38, delete:

" 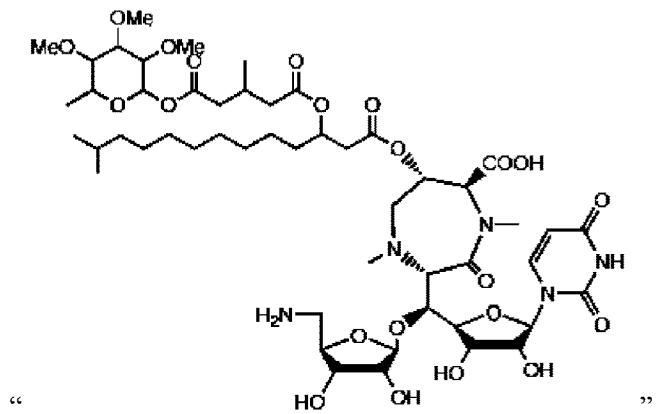 "

And insert:

-- 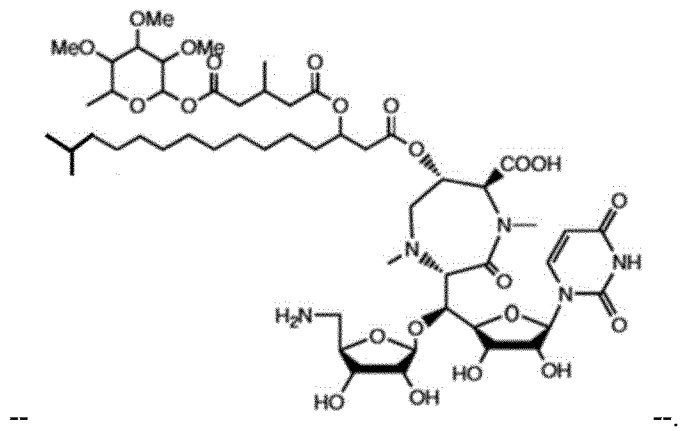 --.

Signed and Sealed this  
Thirteenth Day of November, 2018

Andrei Iancu  
*Director of the United States Patent and Trademark Office*

CERTIFICATE OF CORRECTION (continued)
U.S. Pat. No. 9,839,648 B2

Page 2 of 3

Columns 25 and 26, Lines 2-22, delete:

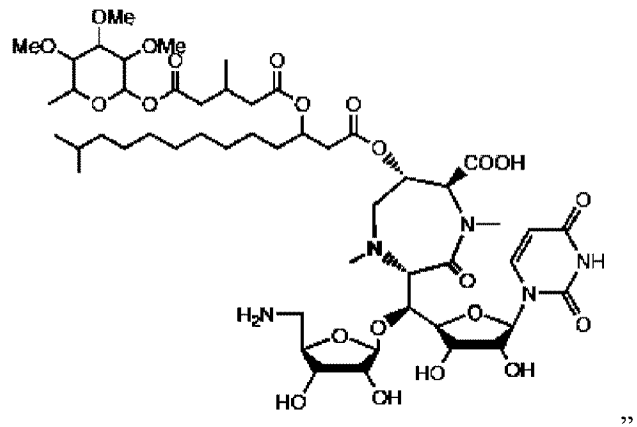

" "

And insert:

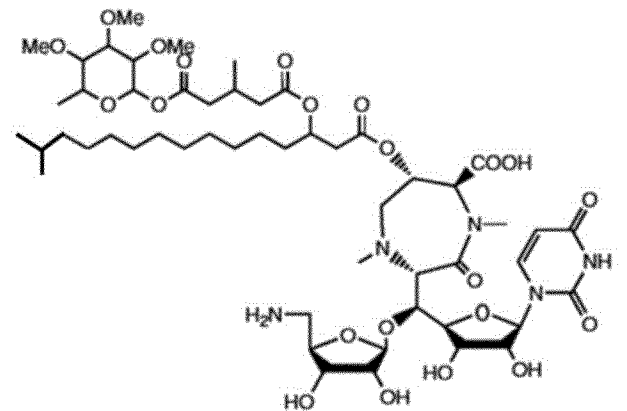

-- --.

In the Claims

Column 38, Lines 18-34, delete:

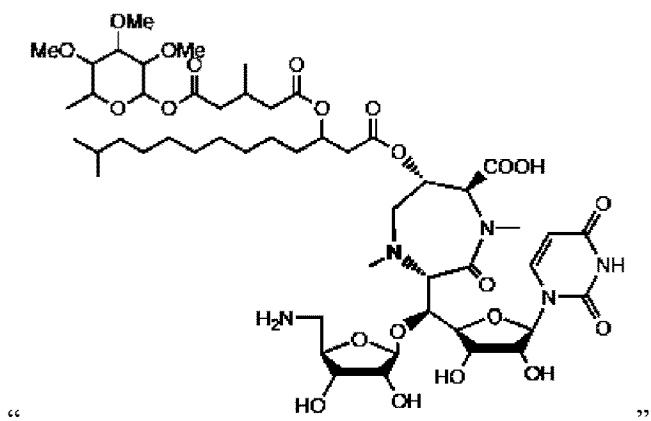

" "

CERTIFICATE OF CORRECTION (continued)
U.S. Pat. No. 9,839,648 B2

And insert:

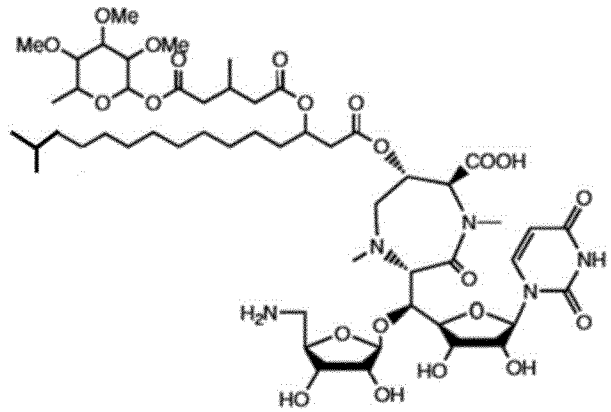

-- --.